United States Patent
Ansari et al.

(10) Patent No.: US 12,431,224 B2
(45) Date of Patent: Sep. 30, 2025

(54) CODING ARCHITECTURES FOR AUTOMATIC ANALYSIS OF WAVEFORMS

(71) Applicant: THE REGENTS OF THE UNIVERSITY OF MICHIGAN, Ann Arbor, MI (US)

(72) Inventors: Sardar Ansari, Richmond, VA (US); Christopher Elliot Gillies, Ann Arbor, MI (US); Kevin R. Ward, Superior Township, MI (US); Hamid Ghanbari, Novi, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1049 days.

(21) Appl. No.: 17/212,799

(22) Filed: Mar. 25, 2021

(65) Prior Publication Data
US 2021/0304855 A1 Sep. 30, 2021

Related U.S. Application Data

(60) Provisional application No. 62/994,545, filed on Mar. 25, 2020.

(51) Int. Cl.
*G16H 10/40* (2018.01)
*A61B 5/00* (2006.01)
*G16H 50/20* (2018.01)

(52) U.S. Cl.
CPC ........... *G16H 10/40* (2018.01); *A61B 5/7264* (2013.01); *A61B 5/7275* (2013.01); *G16H 50/20* (2018.01)

(58) Field of Classification Search
CPC ...... G16H 10/40; G16H 50/20; A61B 5/7264; A61B 5/7275
See application file for complete search history.

(56) References Cited

U.S. PATENT DOCUMENTS

| 8,005,531 B2 | 8/2011 | Xue et al. |
| 8,494,621 B2 | 7/2013 | Xue et al. |
| 10,602,942 B2 | 3/2020 | Shakur et al. |

OTHER PUBLICATIONS

G. Y. H. Lip et al., "Atrial fibrillation," *Nat Rev Dis Primers*, vol. 2, No. 1, p. 16016, Dec. 2016.
Developed with the special contribution of the European Heart Rhythm Association (EHRA) et al., "Guidelines for the management of atrial fibrillation: The Task Force for the Management of Atrial Fibrillation of the European Society of Cardiology (ESC)," *European Heart Journal*, vol. 31, No. 19, pp. 2369-2429, Oct. 2010.
G. V. Naccarelli, H. Varker, J. Lin, and K. L. Schulman, "Increasing Prevalence of Atrial Fibrillation and Flutter in the United States," *The American Journal of Cardiology*, vol. 104, No. 11, pp. 1534-1539, Dec. 2009.
I. Savelieva and J. Camm, "Update on Atrial Fibrillation: Part I," *Clin Cardiol*, vol. 31, No. 2, pp. 55-62, Feb. 2008.
Y. Xia, N. Wulan, K. Wang, and H. Zhang, "Detecting atrial fibrillation by deep convolutional neural networks," *Computers in Biology and Medicine*, vol. 93, pp. 84-92, Feb. 2018.
B. Pourbabaee, M. J. Roshtkhari, and K. Khorasani, "Deep Convolutional Neural Networks and Learning ECG Features for Screening Paroxysmal Atrial Fibrillation Patients," *IEEE Trans. Syst. Man Cybern, Syst.*, vol. 48, No. 12, pp. 2095-2104, Dec. 2018.
S. P. Shashikumar, A. J. Shah, Q. Li, G. D. Clifford, and S. Nemati, "A deep learning approach to monitoring and detecting atrial fibrillation using wearable technology," in 2017 IEEE EMBS International Conference on Biomedical & Health Informatics (BHI), Orland, FL, USA, 2017, pp. 141-144.

*Primary Examiner* — Jerry Lin
(74) *Attorney, Agent, or Firm* — MARSHALL, GERSTEIN & BORUN LLP

(57) ABSTRACT

A method includes receiving raw input signals, analyzing the raw signals using a trained coding architecture including an encoding layer; and displaying an output. A computing system includes a processor and a memory storing instructions that when executed by the processor, cause the computing system to receive raw input signals, analyzing the raw signals using a trained coding architecture and display an output. A non-transitory computer readable medium includes program instructions that when executed cause a computer to receive raw input signals, analyze the raw signals using a trained coding architecture and display an output.

20 Claims, 13 Drawing Sheets

CODING ARCHITECTURES FOR AUTOMATIC ANALYSIS OF WAVEFORMS

CROSS-REFERENCE TO RELATED APPLICATIONS

The present application claims priority to U.S. Provisional Patent Application No. 62/994,545, filed on Mar. 25, 2020, hereby incorporated by reference in its entirety.

FIELD OF THE DISCLOSURE

The present disclosure is generally directed to methods and systems for automatic analysis of waveforms, and more particularly, for processing one or more raw input signals corresponding to a patient using one or more coding architectures to determine one or more condition corresponding to the patient.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

There are massive amounts of waveforms being collected every day using hospital bedside monitors, arterial catheters, Holter devices, photoplethysmography (PPG) sensors, ECG patches, smartphones, smartwatches, etc. The majority of this data is stored without being closely inspected. The interpretation and annotation of the waveforms require a trained physician to closely inspect them, which is time-consuming, labor-intensive, and expensive.

Besides, it is practically impossible for physicians to read and analyze all of the acquired waveforms manually. This greatly limits the usage of waveform for the real-time diagnosis and prognosis of cardiac and other conditions, losing an enormous amount of valuable information that is contained within the waveforms. Hence, there is great interest in the automatic interpretation of physiological waveforms to facilitate prediction, diagnosis and/or monitoring of acute and chronic conditions and overall health.

Conventional techniques for analysis of physiological waveforms are severely limited by, for example, being dependent on the prediction/diagnosis of specific conditions or outcomes. For example, existing techniques may collect 12-lead electrocardiogram (ECG) data and an algorithm may be selected to analyze the ECGs to produce a patient diagnosis. However, conventional techniques lose an enormous amount of valuable information that is contained within the waveforms if that information is not relevant to the classification/regression task. As a result, the generated models cannot be utilized in other applications such as diagnosis of other conditions.

Further, conventional techniques that seek to compress voluminous data (e.g., ECG data) by mapping the data to a lower dimensional space (e.g., principal component analysis) may discard information from an initial data set, rendering the initial data set not useful or less useful for downstream processing. Conventionally, autoencoders may be used to perform feature extraction. However, the focus of conventional autoencoders is in connection to image analysis. As such, conventional autoencoders fail to leverage features that are specific to physiological waveforms. Existing modeling approaches do not take into account the signal periodicity, and for example, conventional autoencoders may not be able to extract the information that is needed for the analysis of heart arrhythmia. Still further, existing approaches that do not analyze raw input signals (i.e., native waveforms) are not able to generate a full range of features due to information lost through various filtering and segmentation routines, and as such, these existing approaches are deficient.

AFib is the most common sustained heart rhythm disorder in the U.S., impacting 1-2% of the general population and 5-15% of those over 80 years of age. AFib is associated with risk of death, stroke, hospitalization, heart failure and coronary artery disease, leading to significant levels of mortality and morbidity. The prevalence of AFib is expected to increase by threefold in the next 30-50 years.

Coronary artery disease (CAD), including stable angina, unstable angina, myocardial infarction, and sudden cardiac death is one of the leading causes of mortality, resulting in more than 8 million deaths globally every year. CAD occurs due of insufficient supply of blood to the heart, leading to ischemia of the cardiac cells. If the ischemia persists, it can lead to permanent damage to the cardiac muscle, causing a myocardial infarction (i.e., a heart attack).

The high frequency of false alarms in various clinical units, including intensive care units has created an "alarm fatigue", i.e., caregivers become desensitized to the alarm sounds, leading to delayed or lack of timely response. Some studies shown that 80% of alarms in perioperative settings were clinically non-consequential. Another study concluded that nearly 72% to 99% of all alarms were false. Most alarms are triggered by algorithms that use waveforms as input.

Hence, there is a great need to substantially increase the accuracy of conventional techniques, to address the problems of arrhythmias, CAD and false alarms. Other conditions are of interest in addition to arrhythmias, CAD and false alarms. For example, traumatic shock and trauma-related infections can result in sepsis, which significantly contributes to mortality and is a major challenge in various clinical settings (e.g., in military medicine and in civilian medicine). Statistically, two in three patients who die in a hospital have sepsis. Currently, sepsis is difficult to diagnose, relying on overt symptoms of systemic illness (e.g., temperature, blood pressure, and heart rate) and an indication of an infectious organism via microbial culture of clinical samples. This difficult diagnosis is problematic because after the onset of sepsis, the effectiveness of intervention with antibiotics or other therapeutics rapidly diminishes, and mortality increases when antibiotic administration is delayed. It is thus imperative that clinicians correctly and timely predict sepsis and clinical deterioration.

The increasing number of heart failure patients has created a pandemic and a major global health problem which is likely to continue growing. Accurate identification of patients at risk of heart failure could allow for lifestyle changes and preventive measures to delay the onset of the disease and improve outcomes. However, conventional techniques are inadequate. The conventional techniques are unable to reliably analyze periodic input signals. Known conventional techniques that analyze ECG information using an autoencoder are only capable of handling a single pre-aligned ECG beat. Conventional techniques that apply an autoencoder to a single ECG beat include additional steps (e.g., QRS detection, beat extraction, preprocessing, etc.) that are costly in terms of storage and computation, resulting in such techniques being impractical in thin client devices. Moreover, the additional processing steps are prone to errors and can lead to reduced system performance. For example, an approach that requires pre-alignment of individual beats requires a beat detection step. However, different patients can have different ECG morphologies due to cardiac conditions, arrhythmias and inter-personal variability. This results in errors in beat detection and consequently in the output of the autoencoder model. Further, certain conditions that require beat plurality for diagnosis (e.g., bigeminy, trigeminy, etc.) are not addressable using known single-beat techniques. Thus, while some conventional techniques may be able to detect HF in some limited circumstances, more robust techniques are needed for detecting HF in patients that lack overt clinical manifestations.

SUMMARY OF THE INVENTION

In one aspect, a computer-implemented method for processing one or more raw input signals corresponding to a patient to determine one or more condition corresponding to the patient includes receiving, via one or more processors, the raw input signals, analyzing, via the one or more processors, the raw input signals using a trained coding architecture to generate a plurality of embedded features corresponding to a reduced dimensionality representation of the raw input signals, wherein the trained coding architecture includes an encoder comprising one or more encoding layers. The method may further include displaying an output corresponding to the embedded features corresponding to the reduced dimensionality representation of the raw input signals in an output device.

In another aspect, a computing system includes one or more processors; and one or more memories storing instructions that, when executed by the one or more processors, cause the computing system to receive, via one or more processors, raw input signals, analyze, via the one or more processors, the raw input signals using a trained coding architecture to generate a plurality of embedded features corresponding to a reduced dimensionality representation of the raw input signals, wherein the trained coding architecture includes an encoder comprising one or more encoding layers. The one or more memories may include further instructions that, when executed by the one or more processors, cause the computing system to display an output corresponding to the embedded features corresponding to the reduced dimensionality representation of the raw input signals in an output device.

In yet another aspect, a non-transitory computer readable medium includes program instructions that when executed, cause a computer to receive, via one or more processors, raw input signals, analyze, via the one or more processors, the raw input signals using a trained coding architecture to generate a plurality of embedded features corresponding to a reduced dimensionality representation of the raw input signals, wherein the trained coding architecture includes an encoder comprising one or more encoding layers. The non-transitory computer readable medium may include further instructions that when executed, cause a computer to display an output corresponding to the embedded features corresponding to the reduced dimensionality representation of the raw input signals in an output device.

BRIEF DESCRIPTION OF THE DRAWINGS

The figures described below depict various aspects of the system and methods disclosed therein. It should be understood that each figure depicts one embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

For a more complete understanding of the disclosure, reference should be made to the following detailed description and accompanying drawing figures, in which like reference numerals identify like elements in the figures, and in which.

Figure 1:
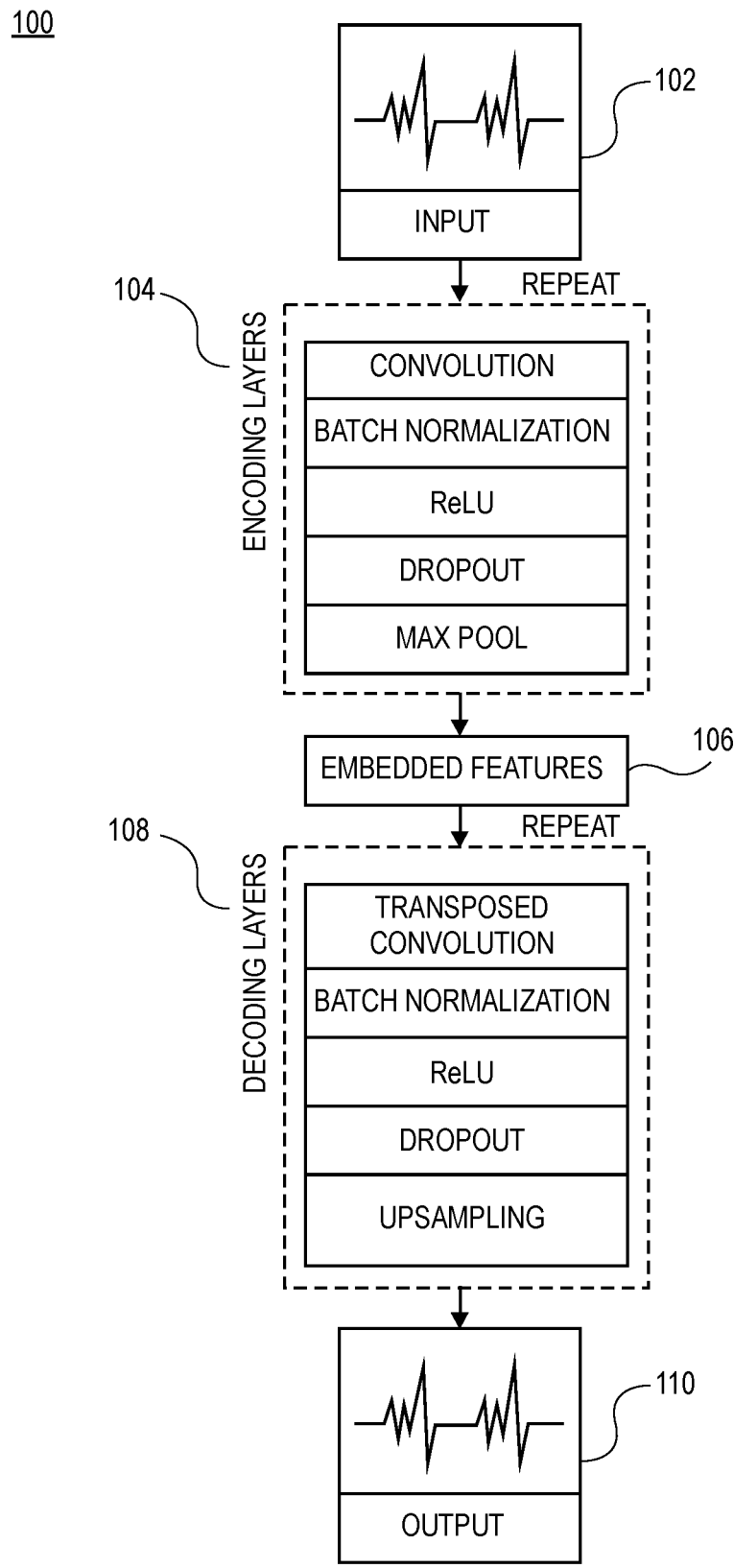
FIG. 1 depicts an exemplary block diagram depicting an exemplary coding architecture, according to one embodiment.

The figures depict preferred embodiments for purposes of illustration only. One of ordinary skill in the art will readily recognize from the following discussion that alternative embodiments of the systems and methods illustrated herein may be employed without departing from the principles of the invention described herein.

DETAILED DESCRIPTION

Overview

The embodiments described herein relate to, inter alia, methods and systems for automatic analysis of waveforms using machine learning techniques that may be used in a variety of different applications. Generally, the present techniques include automatic interpretation of physiologic signals to facilitate identification, prediction and/or diagnosis of acute and chronic conditions and overall health. Herein, a "waveform" may include, but is not limited to, an electrocardiogram (ECG) waveform, an arterial blood pressure (ABP) waveform, a photoplethysmogram (PPG) waveform, an impedance waveform, a piezoelectric-derived waveform, an electroencephalograph (EEG) waveform, etc.

In general, the present techniques may be used to model any periodic physiological input signal. The present techniques use coding architectures (e.g., including an encoder and/or a decoder) that are designed to convert one or more physiologic signals into a more compact and meaningful representation suitable for downstream analysis by clinicians and/or algorithms (e.g., a machine learning algorithm). The term "bottleneck model" may be used to refer to the methods and systems for transforming high-dimensional signals to such compact representations. In some embodiments, the more compact representation may be used to generate visualizations and/or interpretations of physiological signal data to aid patients and caregivers with diagnosing and understanding patient conditions.

Unlike conventional techniques that rely on pre-aligned single ECG beat processing, the present techniques may act on raw ECG signals. No preprocessing of the input waveform is required, enabling the present techniques to use combinations and configurations of machine learning techniques (e.g., recurrent neural networks, convolutional neural networks, etc.) that enable the temporal aspect of ECG data to be fully modeled. Specifically, no match filtering of ECG data is required. No segmentation, such as QRS detection, of ECG data is required. The present techniques enable time and phase features, as well as morphology features to be extracted, as well as for multiple encoders to be used for modeling differing aspects of the input signal. Thus, the architectures included in the present techniques represent an improvement over conventional ECG signal detection methods and systems, by enabling raw data to be processed using significantly more advanced modeling techniques. The architectures represent further improvements due to integration with electronic health records and richer data sets, leading to more robust modeling.

The present techniques are generally applicable to analyzing arrhythmia. For example, the present techniques may be used to detect, predict and/or monitor cardiac arrhythmia (e.g., bradycardia, premature atrial, ventricular contractions, junctional contractions, atrial tachycardia, ventricular tachycardia, junctional tachycardia, multifocal atrial tachycardia, supraventricular tachycardia, atrial flutter, atrial fibrillation (AFib), ventricular fibrillation, wandering atrial pacemaker, AV nodal reentrant tachycardia, junctional rhythm, accelerated idioventricular rhythm, monomorphic ventricular tachycardia, polymorphic ventricular tachycardia, torsades de pointes, arrhythmogenic right ventricular dysplasia, re-entry ventricular arrhythmia, first degree heart block, second degree heart block, third degree heart block, premature atrial contraction (PAC), premature ventricular contraction (PVC), ectopic atrial rhythm, bundle branch block, sinus node dysfunction, sinus arrest, asystole, bigeminy, trigeminy, etc.). It should be appreciated that the foregoing list of cardiac arrhythmia is for exemplary purposes only, and that analyzing other disease conditions (e.g., diseases having viral causes) is envisioned.

Furthermore, the present techniques include diagnosis, prediction and/or monitoring of diseases including coronary artery disease, cardiac arrest (including but not limited to myocardial infarction (MI) and stroke/ischemia), heart failure (HF), sepsis, acute respiratory distress syndrome (ARDS), respiratory failure, trauma, hemodynamic changes and/or hemorrhage. Conventional techniques for analyzing ECG data do not contemplate electronic health records integration or enable any diagnosis or prediction of complex disease states not generally associated with arrhythmias. Furthermore, the present techniques may be used to perform monitoring of non-disease states (e.g., sleep).

The present techniques are outcome-agnostic, in that the methods and systems disclosed herein may learn to understand underlying patterns corresponding to healthy and unhealthy signals. The coding architectures in the present techniques may learn to compress features of periodic signals (e.g., an ECG) without losing information. As a result, the present techniques may be used to conduct large-scale analyses of widely available unread signals regardless of the presence or absence of any particular underlying medical disease/condition.

The present techniques advantageously enable the analysis of many (e.g., tens of millions of ECG signals or more) to create a lower-dimensional representations that may be used for various purposes, including alarm management, arrhythmia analysis, heart failure detection, etc. across multiple patient cohorts to determine current status and/or make predictions about a future state. In general, any bottleneck model that maps input signals back to an original waveform may be used in envisioned embodiments of the present techniques. In other words, any model that includes restrictions causing the model to learn a reduced representation of an input signal may be used.

The present techniques may take advantage of the periodicity that exists in the signal, a feature that is lacking in conventional techniques. For example, many physiological waveform contain cardiac or respiratory cycles that can be modeled efficiently and effectively with the models that are disclosed here. The waveforms analyzed by the present techniques may include waveforms with persistent sampling intervals (e.g., ECG, ABP, etc.). The waveforms may include many samples (e.g., 200 samples/minute or more). The present techniques are applicable in the analysis of any periodic signals (e.g., those generated by a wearable ECG monitor). The present techniques may be used in the detection of various cardiac conditions (e.g., seizures) and for alarm generation and nose reduction, in addition to other techniques.

Various data science modeling and/or machine learning techniques now known or later developed may be used to implement the coding architectures and classifiers discussed herein. Further, the embedded features discussed herein may be created using any now known or later developed techniques.

The trained models may be used for many purposes. For example, in some embodiments, a trained model may learn weights that remain frozen. In some embodiments, an encoding portion of the trained model may be integrated into another model that refines features/weights of the trained model as part of a machine learning process.

Exemplary Coding Architecture

FIG. 1 depicts an exemplary block diagram depicting a coding architecture 100. The coding architecture 100 includes an input layer 102, one or more encoding layers 104, an embedded features layer 106, one or more decoding layers 108, and an output layer 110. The coding architecture 100 may be configured as a deep or shallow artificial neural network, for example. In some embodiments, the coding architecture 100 may be configured as a convolutional or non-convolutional artificial neural network. In still further embodiments, one or more alternative machine learning and/or data science and/or artificial intelligence models may be used to implement the coding architecture 100.

The input layer 102 receives an input signal corresponding to a physiologic system. For example, the input signal may be continuous, discrete, sinusoidal, periodic, aperiodic, etc. The input signal may correspond to an ECG, ABP, PPG, EEG or any other physiologic signal, singularly or in any combination, in some embodiments. The input signal may include a time dimension and be, for example, a fixed-time interval (e.g., a three-second signal, a five-second signal, etc.). The input signal may be of a uniform or variable duration. In an embodiment, input signal windows may be analyzed. For example, when a uniform input signal is N seconds, only N/10 seconds may be analyzed. In another embodiment, a predetermined number of seconds may be sampled (e.g., one second). In another embodiment, a sliding window may be used to analyze the input signal (e.g., ten seconds window). The input layer 102 may pass the input signal to the encoding layers 104. The input signal received by the input layer 102 may be a digital or analog signal, depending on the embodiment and scenario. For example, the input signal may be transmitted by a monitor that emits analog waveforms, or a digitally-encoded signal. The input signal may be a raw data signal, that is not filtered or segmented in any way.

The encoding layers 104 may analyze the input signal. For example, those of ordinary skill in the art will appreciate that the encoding layers 104 may include one or more constituent processing layers, such as a convolution layer, a batch normalization layer, an activation functions (e.g. tanh, ReLU, Leaking ReLU, ELU, SELU, etc.), a dropout layer, a max pooling layer, etc. In addition, the layers may be connected to each other in a linear fashion (the layers being stacked on top of each other, with the output of each layer being fed into the next layer as input) or in a non-linear fashion with feedback, lateral, circular or skip connections (for example, residual connections similar to those in residual neural networks). In some embodiments, a recurrent autoencoder may be used. One or more fully-connected layers may be included in the encoding layers 104.

Training data may be used to train the coding architecture 100 to learn a compact representation of an input signal. The compact representation may be integrated with lab data and vital sign data. Specifically, a machine learning training module (e.g., in the computing device 506 depicted in FIG. 5) may use a supervised or unsupervised deep learning method to create a compact representation of a signal using a large database of signals (e.g., >1 million signals). The coding architecture 100 may learn to copy its input to its output. During this process, the coding architecture 100 learns a low dimensional compact representation corresponding to input waveforms through a combination of linear and nonlinear transformations, which can be thought of as a nonlinear principal component analysis. The low dimensional representations contain a rich nonlinear compression of the signal window that allows a classifier to predict conditions (e.g., sepsis and deterioration). One or more trained models may be stored in any suitable data storage device.

In general, the encoding layers 104 generate embedded features 106 that are a reduced-dimensionality representation of the input signal. In some embodiments, the embedded features 106 may include a nonlinear representation of the input signal. The embedded features 106 may be consumed by one or more decoding layers 108. In other embodiments, multiple encoding layers 104 may be present, where each layer represents one aspect of the representation, e.g., one embedding layer 104 may encode the morphological features of the ECG beats while another embedding layer 104 represents the location of each beat. In another embodiment, several different pathways (encoder and embedding layers) may be utilized in parallel to model different types of components in the waveform, e.g., to model different types of arrhythmia present in an ECG signal.

The coding architecture 100 may be trained using one or more data sets of unlabeled ECGs. For example, a machine learning (ML) training module may train the coding architecture 100 to reconstruct the unlabeled ECGs, to learn intrinsic features of waveforms comprising the ECGs. The training may cause the coding architecture 100 to transform the raw high-dimensional signal of each ECG into a low-dimensional (i.e., more compact) representation. In some embodiments, the ML training module may use the more compact representation to train a further supervised model to predict a specific condition or outcome. In an embodiment, the trained coding architecture 100 may be used to identify/classify clusters of healthy and unhealthy patients. A further process may analyze the clusters by, for example, informing the patients of potential health risks.

Figure 3:
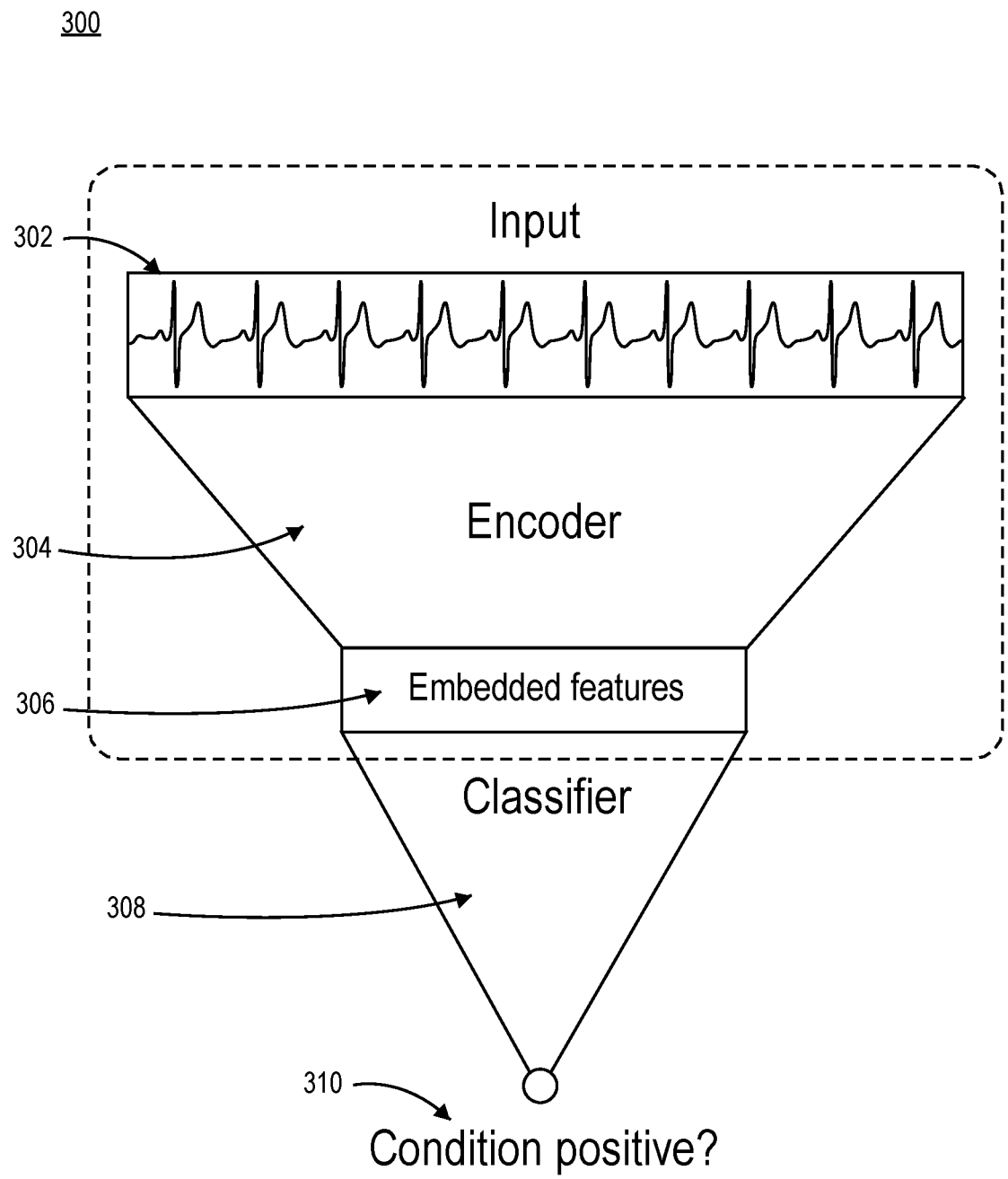
FIG. 3 depicts a block diagram of an exemplary coding architecture classifier that corresponds to a trained model in FIG. 2A, according to an embodiment.

The coding architecture 100 is discussed further with respect to FIG. 3. Generally, the coding architecture 100 accepts a signal of a duration (e.g., three seconds, five seconds, etc.) and converts the signal to a lower dimensional space (e.g., from 380 points to 30 points). A second network (decoder) may convert the lower dimensional space back to the higher space, i.e., reconstruct the input signal. The difference between the input and the reconstructed signal in the output may be measured as autoencoder error, and minimized. Alternatively, the similarity between the input and output signals can be measured via a metric (e.g., correlation) and maximized. In some embodiments, a projection method (e.g., t-distributed stochastic neighbor embedding (TSNE)) may be used to project the lower dimensional ECG into a lower dimensional (e.g., two dimensional) space to identify clusters of patients (e.g., A-fib patients). In some embodiments, noise may be detected, measured and removed from signals using the coding architecture 100. Noise detection/removal may be an advantageous feature, especially in cases where existing false positives present clinical challenges.

In some embodiments, the encoding layers 104 may be thought of as a general-purpose feature extraction tool. As a result, the coding architecture 100 is applicable to many specific medical applications. For example, the representation contained in embedded features 106 may include features that correspond to the timing, height and width of ECG P, Q, R, S, T and U waves. As a result, the coding architecture 100 may be used for detection of cardiac arrhythmia (e.g., AFib, ventricular tachycardia, heart block, atrial fibrillation, etc.), HRV analysis and/or detection of medical conditions that are associated with changes in HRV such as sepsis, hemorrhage and heart failure.

In addition, the representation contained in embedded features 106 includes information about the morphology of the signal (e.g., ECG, ABP, PPG or others). This information further facilitates classification of different arrhythmia that result in abnormal waveform patterns (e.g., atrial fibrillation, premature ventricular contraction, etc.). Moreover, various medical conditions that impact the morphology of the waveform (e.g., myocardial ischemia, myocardial infarction, hyperkalemia, etc.) can be detected using the embedded features 106. It should be appreciated that the present techniques may be utilized in any task (e.g., detection, classification, clustering, etc.) that involves the medical waveforms (e.g., ECG, ABP, PPG, etc.).

The decoding layers 108 may analyze the embedded features 106. For example, those of ordinary skill in the art will appreciate that the decoding layers 108 may include one or more constituent processing layers/filters, such as a transposed convolution layer, a batch normalization layer, an ReLU layer, a dropout layer/filter, upsampling layer, etc. The architecture of the encoding layers 104 and the decoding layers 108 may differ according to the needs of several embodiments. The architecture of the decoding layers may mirror, or be symmetrical to, that of the encoding layers 104, in that there may be same type and/or number of layers in both the encoding layers 104 and the decoding layers 108. The topology of the coding architecture 100 corresponds to the best representation of the input signal.

In operation, the coding architecture 100 may encode the input signal by a series of blocks (e.g., convolutional blocks) in the encoding layers 104. The encoding layers 104 may have decreasingly smaller sizes, such that the embedded features 106 are of a compressed size. The decoding layers 108 may process the embedded features 106. The decoding layers 108 may include layers of an increasing size culminating in the output layer 110 that outputs a reconstructed output signal of equal size to the input signal. In another embodiment, the reconstructed signal may represent a portion of the input signal (e.g., a single beat on an ECG waveform), which may be subsequently replicated several times to reproduce the input signal.

In some embodiments, residual connections may be used within the coding architecture 100. In that case, parameters of the coding architecture 100 may be adjusted, such as the number of encoding and decoding blocks to use, the size of the filters, number of filters, and the size of the embedded features. For example, in an embodiment, the number of embedded features may be minimized, while also minimizing loss of the coding architecture 100.

It should be appreciated that the discussed examples are for explanatory purposes only and that many further embodiments are envisioned. For example, a variational encoder may be used in some embodiments, with the added benefit of generating data. In some embodiments alternative weight initialization strategies may be used. The embedded features 106 may be determined according to different distributions (e.g., a Gaussian prior distribution leads to a variational coding architecture, while other distributions can be envisioned).

The coding architecture 100 may be trained using a training data set of historical signals. In some embodiments, a portion of the training data set of signals (e.g., 10% of signals from a disjoint set of patients in the training set) may be held out to evaluate and compare coding architectures. Multiple architectures may be compared using, for example, the mean square error between the input signal and the reconstructed output signal.

Once the coding architecture 100 is trained, it can be used for feature extraction from the input signal. Since the transformation from the input signal to the embedded features is reversible, the features contain the entirety of the information that is contained within the input signal. As a result, the embedded features can be used in any downstream unsupervised (e.g., clustering), supervised (e.g., classification or regression) or semi-supervised task, without any loss of information. For example, a coding architecture trained on ECG signals can be used to transform raw ECGs into embedded features, in lower dimensions (more compact than the input), that fully describe the input ECG without any loss of information. This trained coding architecture 100 can be later used in a supervised task such as classification of AFib patients, using a small labeled dataset of ECGs with and without AFib.

In some embodiments, various testing techniques may be used to demonstrate the accuracy of the coding architecture 100. For example, the present techniques may include filtering the training data set to include only signals that have an arrhythmia label. Within the training set, a classification model (e.g., logistic regression, support vector machine, decision trees, random forest, neural network, Bayesian classifiers, k-nearest neighborhood, among others) using the embedded features 106 learned from the coding architecture 100 as input and the class label for a 10-second signal's arrhythmia as the output. A similar model may be trained using the normalized signal as the input, wherein a classification model is trained. Finally, a principal component analysis may be used as a baseline for learning latent structure and for comparison to the convolutional coding architecture 100.

The patient's hemodynamics can be identified in the lower-dimensional representation of the input signals (e.g., ECG, ABP, PPG, etc). This representation, when combined with commonly collected patient vital signs and laboratories, may be used to predict the onset of sepsis and physiologic deterioration in patients significantly better than methods using labs and vital signs alone. The modeling is shown to be more accurate than conventional models that use only labs and vital signs for predicting sepsis and all-cause deterioration. In some embodiments, a time series associated with patient data in the historical dataset of patients may include multiple labels indicating any time when the patient met the criteria for sepsis/septic shock within the time series.

Other adverse events may be indicated in the training data (e.g., transfer to the ICU in a case that otherwise did not meet the septic shock definition). The historical dataset may comprise data representing a large period of time (e.g., spanning five years or more). The historical dataset may include many (e.g., one million or more) ECG signals comprising, for example, 10-second 12-lead signals of at least 120 Hz. In some embodiments, only single-lead data is used to train a more general coding architecture that can be used to analyze waveforms from a variety of sources including ECG patches and intermittent ECGs and other physiologic signals measured by smart watches and wristbands.

The ability of the coding architecture 100 to consume high dimensional data is highly advantageous in a clinical setting. For example, monitoring an overnight patient may generate voluminous ECG data. The overnight patient may experience several bouts of AFib that are detected using the present techniques that may be otherwise undetected. Similarly, the present techniques may be used to identify conditions before those conditions become overt (e.g., sepsis, heart failure, etc.).

In some embodiments, prior distributions are applied to the compact representation 106, forcing the variables in the compact representation 106 to be independent. Similar to variational coding architectures, such prior distributions may be incorporated into an objective function of the coding architecture 100 through a Kullback-Leibler divergence term. As a result, the coding architecture 100 may minimize reconstruction error and the divergence between the distribution of the elements of the code and the predefined prior distribution simultaneously. The resulting coding architecture 100 can produce a compact representation 106 that is easier to interpret by physicians and care providers, increasing the acceptance of the final coding architecture 100.

It is noteworthy that the coding architecture 100 may be trained independent of any specific labels, therefore, it is agnostic to underlying arrhythmia, condition or disease. Hence, the coding architecture 100 can be used in a multitude of different applications beyond sepsis or AFib detection. In addition to eliminating the burden associated with manual labeling of the signals, the present techniques further advantageously reduce the need for engineering features in future applications that depend on the analysis of known waveforms (e.g., ECGs). Such efficiency greatly reduces the computational cost, effort and complexity required for future research projects. Moreover, the coding architecture 100 may be easily scaled and be applied to signals collected using a variety of different devices, including hospital monitors, wearable patches, smartphones and smart watches. Indeed, once trained, the coding architecture 100 may process inputs on peripheral/edge devices (e.g., a smart phone, a smart watch, etc.). One or more frequency parameters may be set based on expected battery usage.

Exemplary Coding Architecture Embodiments for Waveform Analysis

As noted, conventional training of models (e.g., an artificial neural network) to detect, predict and/or monitor a particular disease state requires a large dataset of labeled input data (e.g., ECGs). While unlabeled ECGs are abundant in most medical centers, large labeled datasets are rare. To take advantage of the unlabeled ECGs, the present techniques may use self-supervised modeling, advantageously overcoming the problem of labeled data paucity.

Conventional techniques attempt to predict a specific abnormality or disease. On the other hand, the present techniques include methods and systems for analysis of the waveforms (e.g., ECGs) that result in a low-dimensional representation of the signal that may be used in a variety of downstream tasks (e.g., classification, visualization, etc.). In some embodiments, a coding architecture may transform a signal from a high-dimensionality to a lower dimensionality and then back from the lower dimensionality back to the higher dimensionality. In some embodiments, a coding architecture may perform only dimensionality reduction.

Figure 2A:
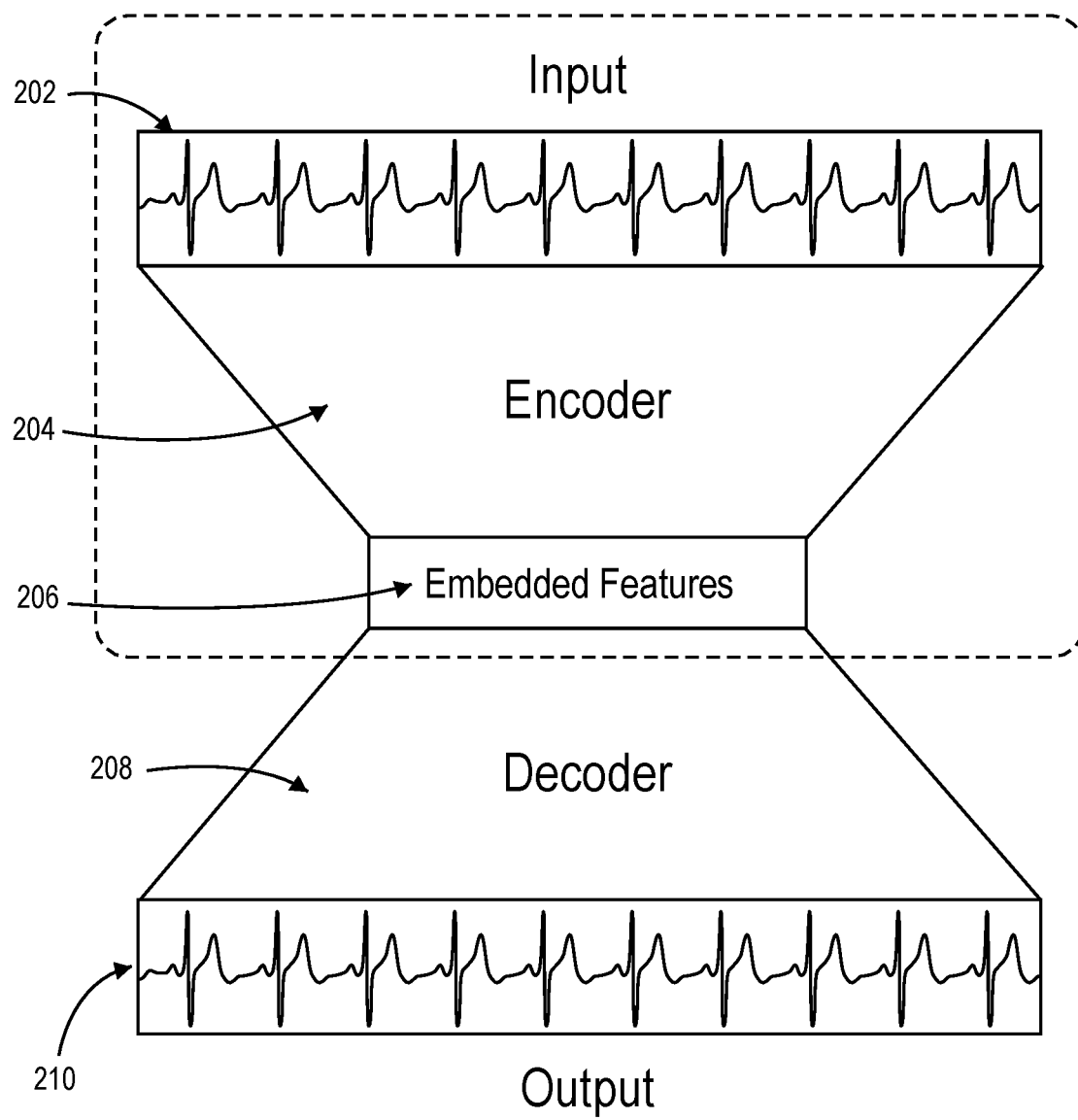
FIG. 2A depicts a block diagram of an exemplary coding architecture used during training, according to one embodiment.

For example, FIG. 2A depicts a block diagram of an exemplary coding architecture 200 wherein an input signal 202 (e.g., an ECG signal) is encoded by an encoder 204 into a low-dimensional compact representation 206 of the input signal 202, according to an embodiment. For example, the encoder 204 may correspond to the encoding layers 104 of FIG. 1. The compact representation 206 may correspond to the embedded features 106 of FIG. 1. The exemplary coding architecture 200 further includes a decoder 208 that may output a reconstructed output signal 210 of equal size to the input signal 202. For example, the decoder 208 may correspond to the decoding layers 108. The reconstructed output signal 210 may correspond to the output 110 of FIG. 1, for example. As with the coding architecture, the coding architecture 200 may be a deep or shallow network, and/or a convolutional and/or non-convolutional network. In some embodiments, the coding architecture 200 may be implemented as a conventional autoencoder.

In some embodiments, a medical center (e.g., Michigan Medicine and its Center for Integrative Research in Critical Care (MCIRCC)) may collect unlabeled ECG data (e.g., thousands or more hours of data corresponding to many thousands of respective patients, or millions of short 12-lead ECGs). The present techniques may leverage the massive unlabeled ECG data to reduce the size of or eliminate the need for labeled datasets for supervised training of a classifier (e.g., an AFib classifier). In some embodiments, a self-supervised learning technique may be combined with transfer learning. A self-supervised technique such as a convolutional autoencoder may be used. A convolutional autoencoder or other machine learning tool may learn a low-dimensional representation of the unlabeled ECG data by training a model that reproduces unlabeled input data using a network architecture that forces information to flow through a bottleneck.

For example, the coding architecture 200 may learn to interpret the input signal 202 by decomposing the input signal 202 into its fundamental components (e.g., the compact representation 206). These fundamental components may be thought of as essential features of a waveform (e.g., an ECG input signal). Hence, the encoder 204 may act as a general-purpose feature extraction tool.

Figure 2B:
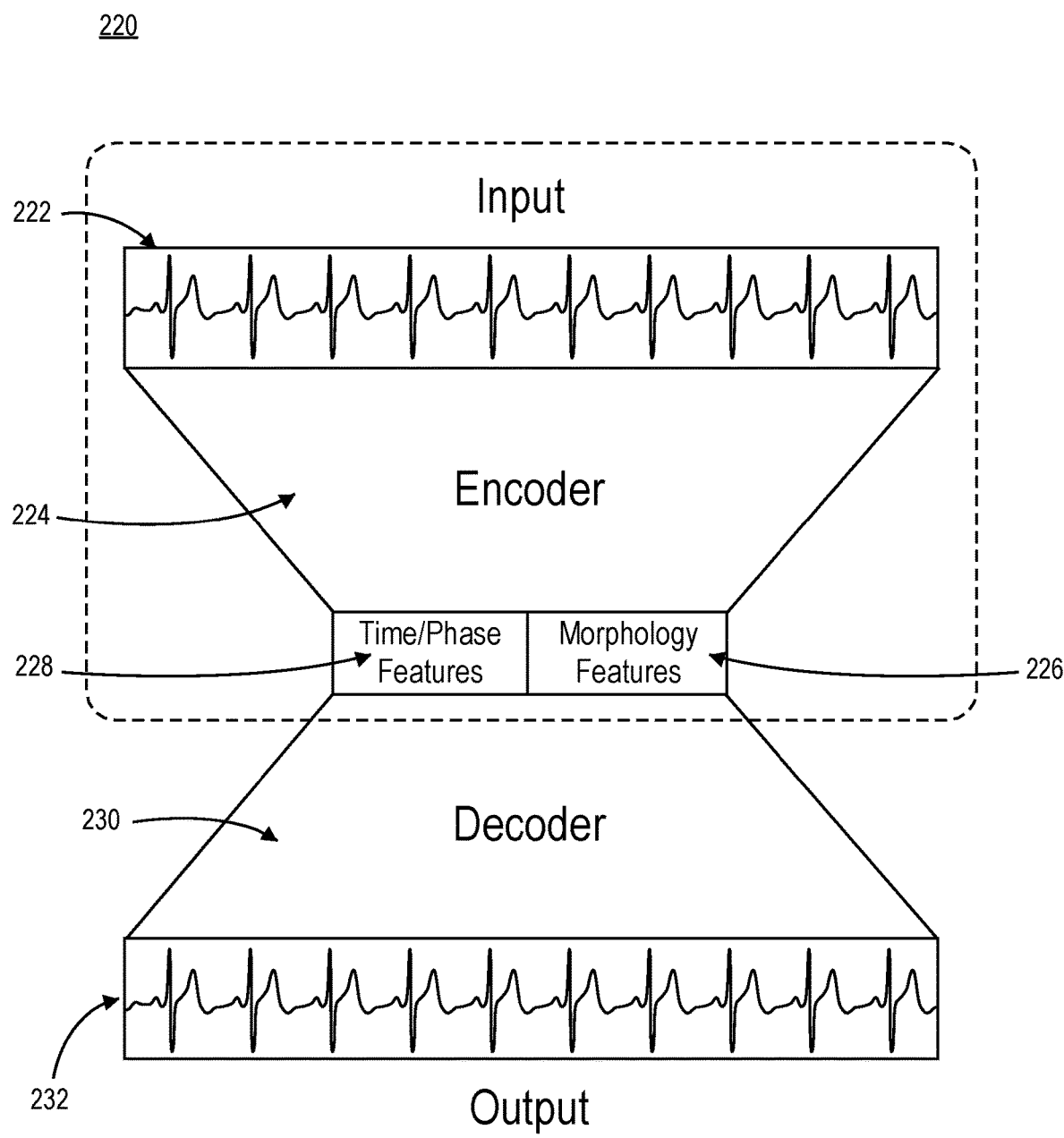
FIG. 2B depicts a block diagram of an exemplary coding architecture used during training including morphological and time/phase separation, according to an embodiment.

The present techniques include additional configurations/embodiments that provide advantages over conventional approaches. For example, FIG. 2B depicts a block diagram of an exemplary coding architecture 220 wherein an input signal 222 (e.g., a periodic waveform) is encoded by an encoder 224 into a low-dimensional compact representation that includes a set of one or more morphological features 226 and a set of one or more time/phase features 228. Advantageously, the coding architecture 220 may leverage the periodicity of physiological input signals. Analyzing periodic input signals is an improvement over known conventional techniques. The coding architecture 220 may capture the morphological features 226 of the input signal 222 (e.g., ECG, onset, provocation, quality, region severity and time (PQRSTU), amplitude, location, etc.) in a first vector, in some embodiments. For example, the morphological features 226 may include heartbeats when the input signal 222 corresponds to an ECG, ABP, or PPG signal.

The coding architecture 220 may capture time/phase features in a second vector. In some embodiments, arrays or other suitable data structures may be used to store the morphological features 226 and/or the time/phase features 228. The time/phase features 228 may represent the timing (or phase) of the output signal 232 and/or the individual components (i.e., periods) of the output signal 232. In some embodiments, the encoder 224 may output both of the morphological features 226 and the time/phase features 228. In some embodiments, a first encoder 224 may be used to output the morphological features 226 and a second encoder 224 may be used to output the time/phase features 228.

Figure 2C:
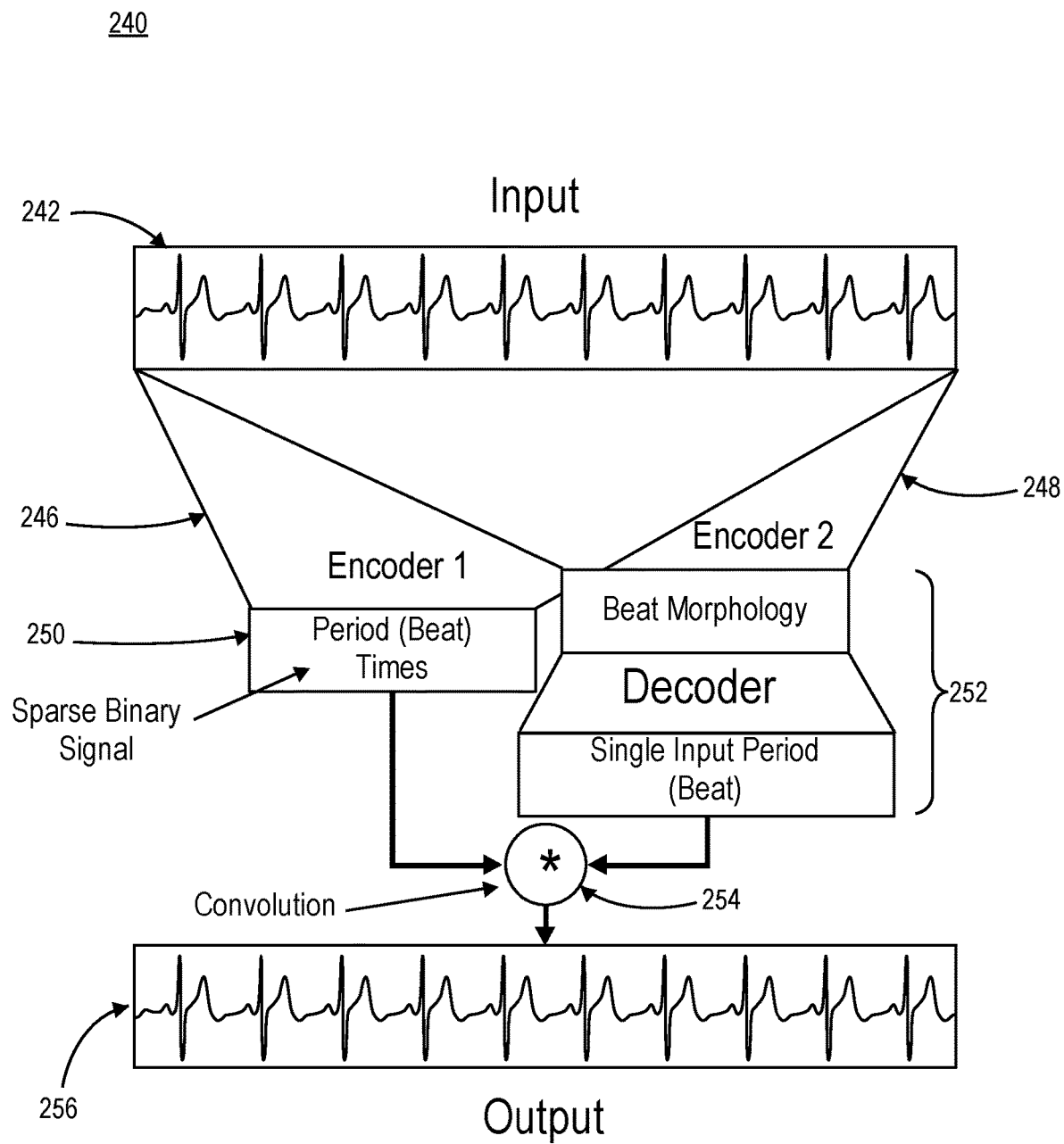
FIG. 2C depicts a block diagram of an exemplary coding architecture used during training including morphological beat and time/phase beat separation, according to an embodiment.

FIG. 2C depicts a block diagram of an exemplary coding architecture 240 wherein an input signal 242 is encoded by a first encoder 246 and a second encoder 248. The first encoder 246 transforms the input signal 242 into period times (i.e., phase) components 250. The second encoder 248 transforms the input signal 242 into period morphology components that a decoder 252 transforms into single input period (beat) of the input signal 242. The period times 250 may be represented in a sparse binary signal (e.g., in a sparse binary vector stored in a memory of a computing device) wherein a value (e.g., 1) indicates the location of beats. The morphology components may contain information representing a single period of the signal (e.g., a heartbeat in the case of ECT, ABP, PPG, etc.). The single input period beat output of the decoder 252 and the period beat times 250 may be analyzed by a convolutional component 254 to generate an output signal 256 that is a reconstruction of the input signal 242. It should be appreciated that in some embodiments the convolutional component 254 may be replaced by any operation that replicates the decoder 252 output in the time domain represented by the period beat times 250, in order to reconstruct the input signal 242.

Figure 2D:
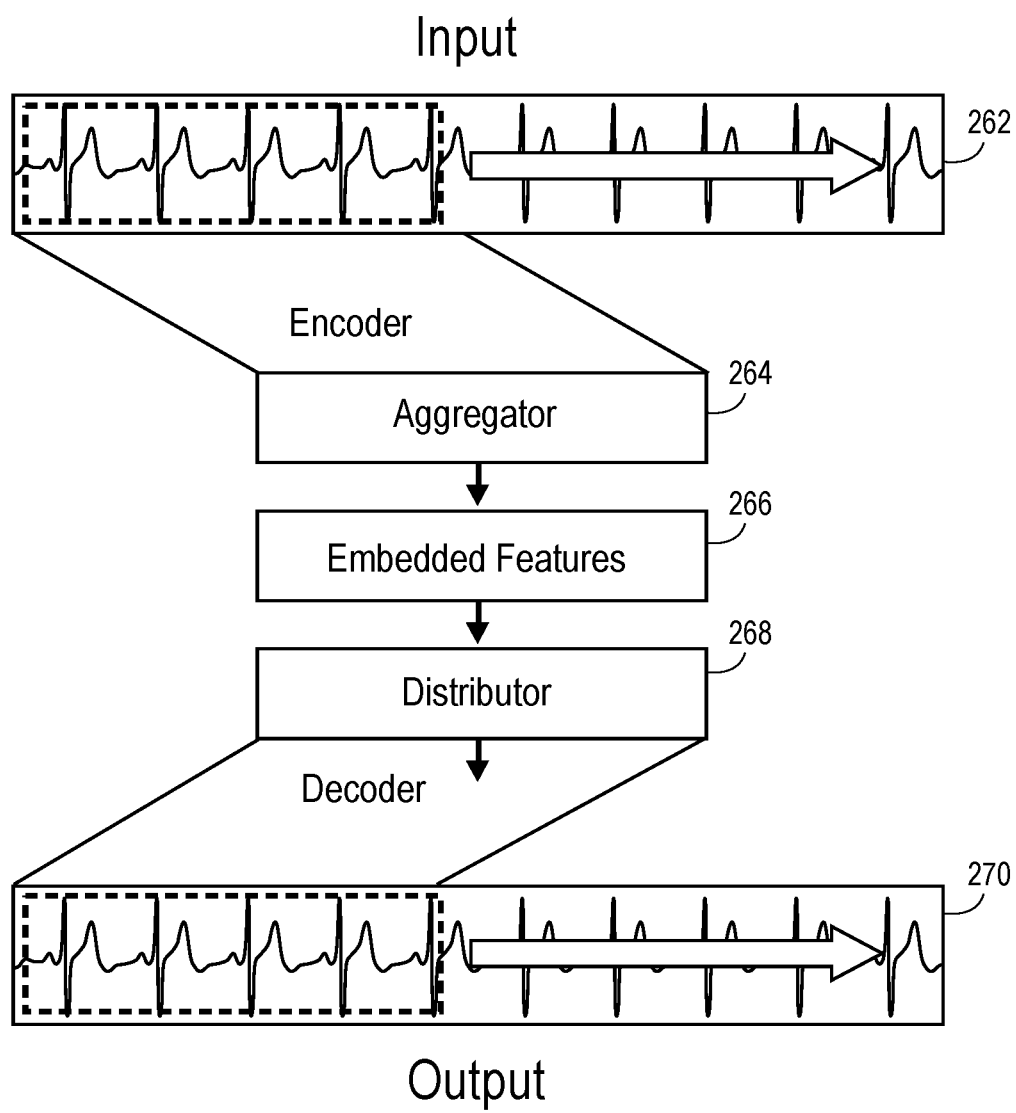
FIG. 2D depicts a block diagram of an exemplary coding architecture used during training including sliding window scanning, according to an embodiment.

FIG. 2D depicts a block diagram of an exemplary coding architecture 260 wherein an input signal 262 includes a plurality of sliding windows. The coding architecture 260 includes an encoder that is mapped by an aggregator 264 to a set of embedded features 266 (e.g., a single vector). For example, the aggregator 264 may be implemented as a many-to-one function. In an embodiment, the aggregator 264 may be implemented as a many-to-one recurrent neural network (RNN). In another embodiment, the aggregator 264 may be implemented as a plurality (e.g., a stack) of many-to-many RNNs followed by a many-to-one RNN.

The coding architecture 260 further includes a distributor 268 that maps the embedded features 266 to a decoder. The distributor 268 may be implemented as a one-to-many function that maps the embedded features 266 back to a sequence of sliding windows composing an output signal 270 as reconstruction of the input signal 262. For example, in an embodiment, the distributor 268 may be implemented as a one-to-many RNN. In another embodiment, the distributor 268 may be implemented as a one-to-many RNN followed by a plurality (e.g., a stack) of many-to-many RNNs. It should be appreciated that other implementations of the aggregator 264 and the distributor 268 are envisioned, such as implementations that incorporate functions (e.g., sum, mean, etc.). It should also be appreciated that the embedded features 266 may be represented using any suitable data structures (e.g., as scalar values, a vector, a multi-dimensional array, etc.).

In an alternative embodiment to FIG. 2D, the position of the encoder and aggregator and/or the position of the distributor and decoder may be swapped. For example, the plurality of windows of the input signal 262 may first be processed by the aggregator 264 (e.g., an RNN, stack of RNNs, aggregator function, etc.) to map the plurality of windows via the encoder to the embedded features 266. The output of the aggregator 264 may then be fed into the encoder and mapped to the embedded features 266. The embedded features 266 may be decoded and then processed by the distributor 268 (e.g., by a one-to-many function such as an RNN or stack of RNNs, etc.).

Figure 2E:
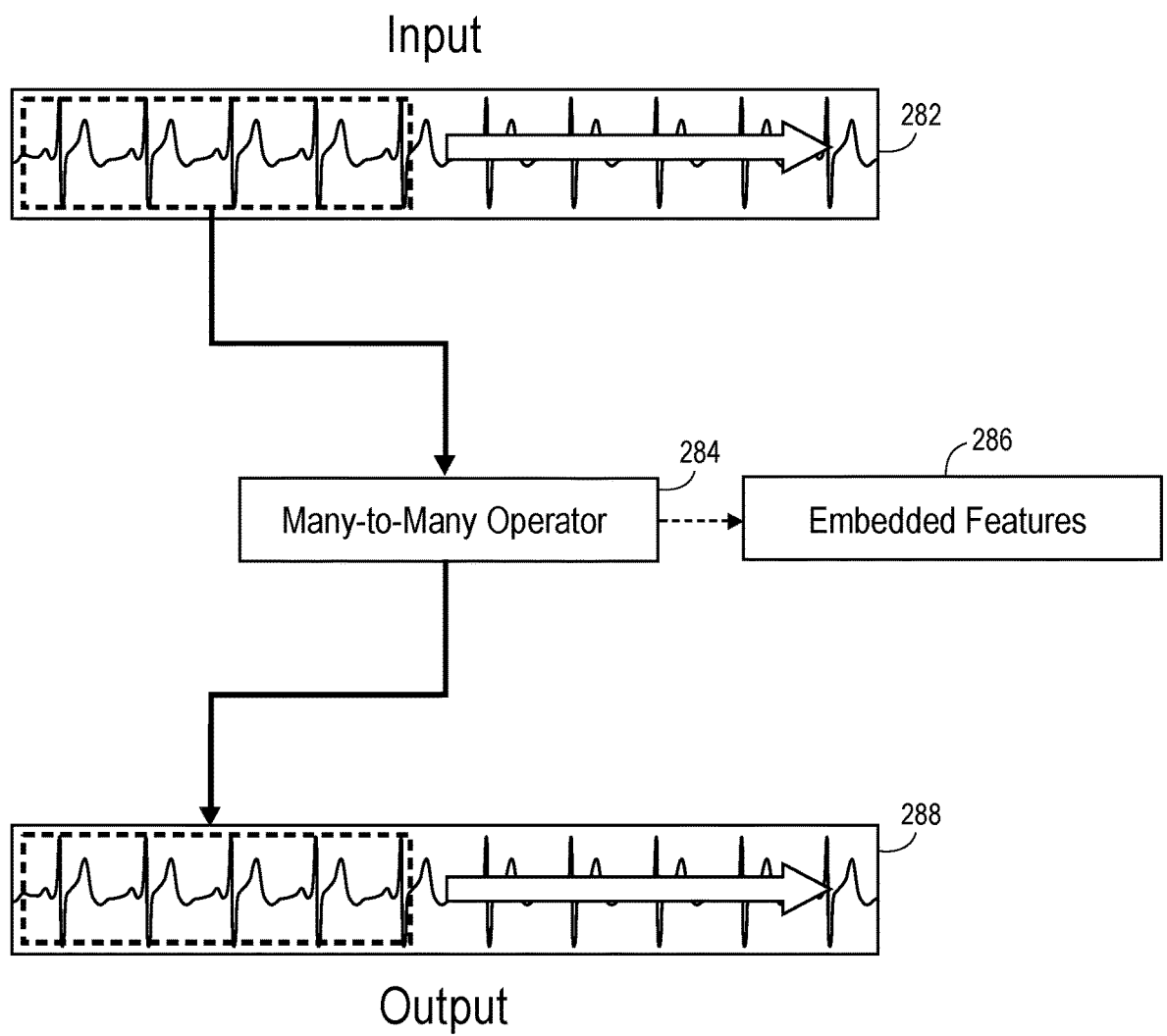
FIG. 2E depicts a block diagram of an exemplary coding architecture used during training including many-to-many mapping applied to a sliding window sequence, according to an embodiment.

FIG. 2E depicts a block diagram of an exemplary coding architecture 280 wherein an input signal 282 includes a plurality of sliding windows (e.g., a sequence). The coding architecture 280 includes a many-to-many operator 284 that maps the plurality of input windows to a sequence of output windows composing an output signal 288. The many-to-many operator 284 may be implemented as an RNN, for example. The many-to-many operator 284 may include one or more state variables corresponding to one or more embedded features 286. It should be appreciated that other embodiments of the coding architecture 280 are envisioned, that include combinations of many-to-one, one-to-many and/or many-to-many networks (e.g., RNNs).

It should also be appreciated that any of the foregoing exemplary coding architectures (e.g., the coding architecture 200, the coding architecture 220, the coding architecture 240, the coding architecture 260, and/or the coding architecture 280), as well as any suitable variations and/or reconfigurations thereof, may be combined to model different aspects of input physiological signals.

Exemplary Compositional Encoding Architecture Embodiments for Waveform Analysis

Figure 2F:
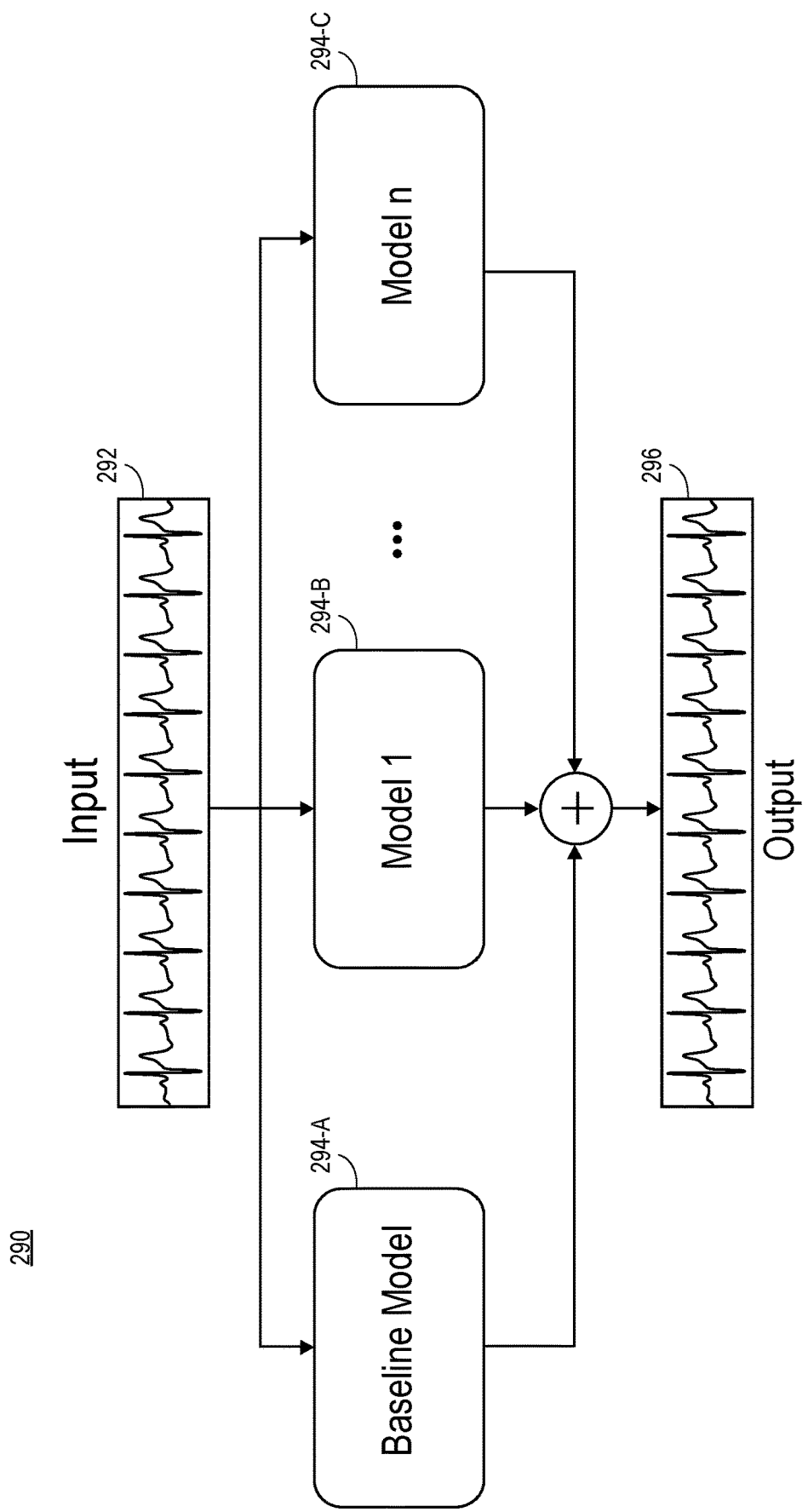
FIG. 2F depicts a block diagram of an exemplary coding architecture used during training including model composition, according to an embodiment.

As noted, the present encoding architectures may be combined/composed to analyze waveforms (e.g., periodic physiological signals). For example, FIG. 2F depicts a block diagram of an exemplary compositional encoding architecture 290. The compositional encoding architecture 290 receives an input signal 292 and includes a plurality of models 294. In some embodiments, the compositional encoding architecture 290 includes a baseline model 294-A. The baseline model 294-A may model the baseline of the input signal 292. For example, the input signal 292 may include low-frequency baseline wander that causes the compositional encoding architecture 290 to recreate the input signal 292. By including a baseline model 294-A, the baseline wander may be removed, allowing the model to correctly model individual beats/features of the input signal 292. Specifically, the baseline model 294-A may capture low-frequency variations in the input signal 292 that are associated with the signal baseline. It should be appreciated that in some embodiments, the baseline model 294-A may be omitted.

The encoding architecture 290 may include a first model 294-B. For example, the first model 294-B may correspond to one of the aforementioned encoding architectures such as the encoding architecture 240. The encoding architecture 290 may include any number (i.e., n) of additional models including a last model 294-C. The models 294 may relate to respectively distinct portions of the input waveform 292. For example, the first model 294-B may relate to a normal sinus rhythm beat in an input ECG window while the nth model 294-C relates to another window (e.g., premature ventricular contraction, etc.). The models 294 may independently model the respective portions of the input signal 292 and reconstruct a respective output. The respective outputs may be combined into an overall reconstructed output waveform 296. It should also be appreciated that one or more of the models 294 may be activated while one or more others are inactivated (e.g., using regularization techniques) to minimize the number of models used to reconstruct a given input signal.

In general, the aforementioned coding architectures may be trained using any suitable loss functions (e.g., mean-squared error, mean absolute error, mean squared logarithmic error, Huber, pseudo-Huber, log cosh, quantile losses, etc.). It should be appreciated that the input signals may be received by any suitable means (e.g., in real-time from a dedicated machine, from a hard disk storage, etc.). It should also be appreciated that a variety of distributions may be imposed on various sections of the coding architectures. For example, a standard normal prior distribution may be imposed on the embedded features 206 of FIG. 2A to create a variational coding architecture. A variety of regularizations may be imposed on various sections of the coding architectures, such as L1 and L2 regularizers. Those of ordinary skill in the art will appreciate that the coding architectures may operate on time domain inputs, frequency domain inputs, wavelet domain inputs, etc.

Exemplary Recurrent Network Embodiments

As discussed, the present techniques may include the use of one or more recurrent neural networks (RNNs) including a long short-term memory (LSTM) network and/or gated recurrent unit (GRU).

In some embodiments, an RNN architecture may learn the embedded representation of the signal. For example, a coding architecture (e.g., the coding architecture 100 of FIG. 1) may receive an input signal and learn an embedded representation of the input signal. RNN coding architectures may use an artificial neural network, deep learning techniques following an autoencoder-like network topology and/or many other machine learning approaches for constructing the embedded representation.

In some embodiments, an RNN may apply the embedded representation/encoding model to a downstream application.

For example, a coding architecture including an RNN may use the learned embedded representation for predicting outcomes of interest by, for example, simplifying using the embedded representation. The embedded representation may be applied in conjunction with labs and other vital signs.

Exemplary Transfer Learning Embodiments

In some embodiments (e.g., wherein an artificial neural network architecture is used) the coding architecture may include frozen weights. In this case, the frozen weights may correspond to a non-linear function that receives the input signal and transforms the input signal to the embedded representation.

In some embodiments, the coding architecture may include unfrozen weights. In this case, the encoding portion of the coding architecture (e.g., the encoder 224 of FIG. 2B) itself is transplanted into a new model (e.g., a coding architecture, or another unrelated model) for downstream applications (e.g., AFib or sepsis detection). The weights of the encoding model may then be refined within the new application's model.

It should be appreciated that the amount of data available for the downstream application may determine whether to use a frozen or unfrozen architecture. For example, using the frozen weight architecture may be more suitable with small amounts of data. Using the unfrozen weight architecture may be more suitable when the downstream application includes higher amounts of data, so that the coding architecture can tailor itself to the specific downstream application more.

Exemplary Classification Embodiment

FIG. 3 depicts an exemplary coding architecture 300 for classifying a condition 310. The coding architecture 300 may include an input signal 302, an encoder 304 and a compact representation 306. The compact representation 306 represents the entirety of the information contained within the original input signal 302 (no loss of information). The compact representation may be received by a classifier 308 (e.g., a classification model, such as a neural network, a support vector machine, a gradient boosting decision tree, etc.) that analyzes the compact representation to output a classification corresponding to the condition 310. For example, the classifier may correspond to a gradient boosting tree. In some embodiments, the coding architecture 300 may correspond to the coding architecture 200, except that the coding architecture 300 lacks a decoder corresponding to the decoder 208 of FIG. 2.

In some embodiments, after training the coding architecture 300, the encoder 304 is detached from the rest of the coding architecture 300 and the output of the encoder 304 (i.e., the compact representation 306) is fed into the classifier 308 to classify the compact representation (e.g., to classify an instance of AFib or the other arrhythmia discussed above). The reduced representation (i.e., a compact representation 306) is smaller in size. Therefore, advantageously, a much smaller labeled dataset is needed for training the classifier 308. In addition to dimensionality reduction and feature extraction, the coding architecture 300 can be used for noise detection and removal. Specifically the coding architecture 300 may be trained using noise-free ECGs.

As a result, the coding architecture 300 may only learn patterns that are associated with true ECG and may learn to eliminate noise components present in the input signal 302. In addition, the error between the input signal 302 and the output signal 310 may be used as a metric for noise level. For example, a large discrepancy between the input signal 302 and the output signal 310 may be indicative of noisy input signal 302. Such a measurement may be particularly useful when the input signal 302 is collected using a noise-prone device (e.g., as ECG patch). In general, filtering noise may be a side-effect of the coding architecture 300, and the reconstructed output of the coding architecture 300 (i.e., the output signal 310) may be cleaner than the original input signal 302. By subtracting the reconstructed output from the original input signal 302, the coding architecture 300 may provide a measure of how much noise appears in the input signal 302, which may be used for noise detection.

Exemplary Self-Supervised Modeling Embodiments for Reduction of False Alarms

In yet further embodiments, the noise detection aspects of the present techniques may be used for further processing of the input signal 302. For example, a deep learning model may be trained to identify noise in the input signal 302. The deep learning model may be used to automatically detect and discard noisy sections of the input signal 302 (e.g., prior to a morphology analysis of the input signal 302). Discarding noise through such automation may detect abnormal beats while reducing false alarms (e.g., an ICU alarm).

In addition, the embedded features can be used to train more accurate and robust classification models for cardiac arrhythmias and other abnormal waveforms that are the source of most alarms. This will lead to a reduction in the number of false alarms. Improving alarm management is very beneficial to patients and caregivers, as false alarms caused by noisy input signals are a major problem in most hospitals today.

Exemplary Sepsis Classifier Embodiment

In an embodiment, a coding architecture (e.g., the coding architecture 100) may be trained to predict the likelihood that a patient will meet the Sepsis-3 or Rhee criteria within a period of time (e.g., within the next three hours). The coding architecture 100 efficiently represents an ECG signal to predict sepsis.

For example, the coding architecture 100 may integrate heterogeneous data to predict the onset of sepsis in advance of a patient developing clinical sepsis. Specifically, the training data may be merged with EHR data, including laboratory results and vital signs, to create a predictive model of sepsis. In some embodiments, training data may be discovered by querying a cohort of patients to identify a number of patients whose historical EHR include ECG data up to 14 days after the start of the hospital encounter, wherein the patients developed sepsis, with concomitant ECG data (e.g., up to 24 hours before the first time sepsis was clinically identified). The data set may be partitioned into training, validation, and test sub datasets.

Figure 4:
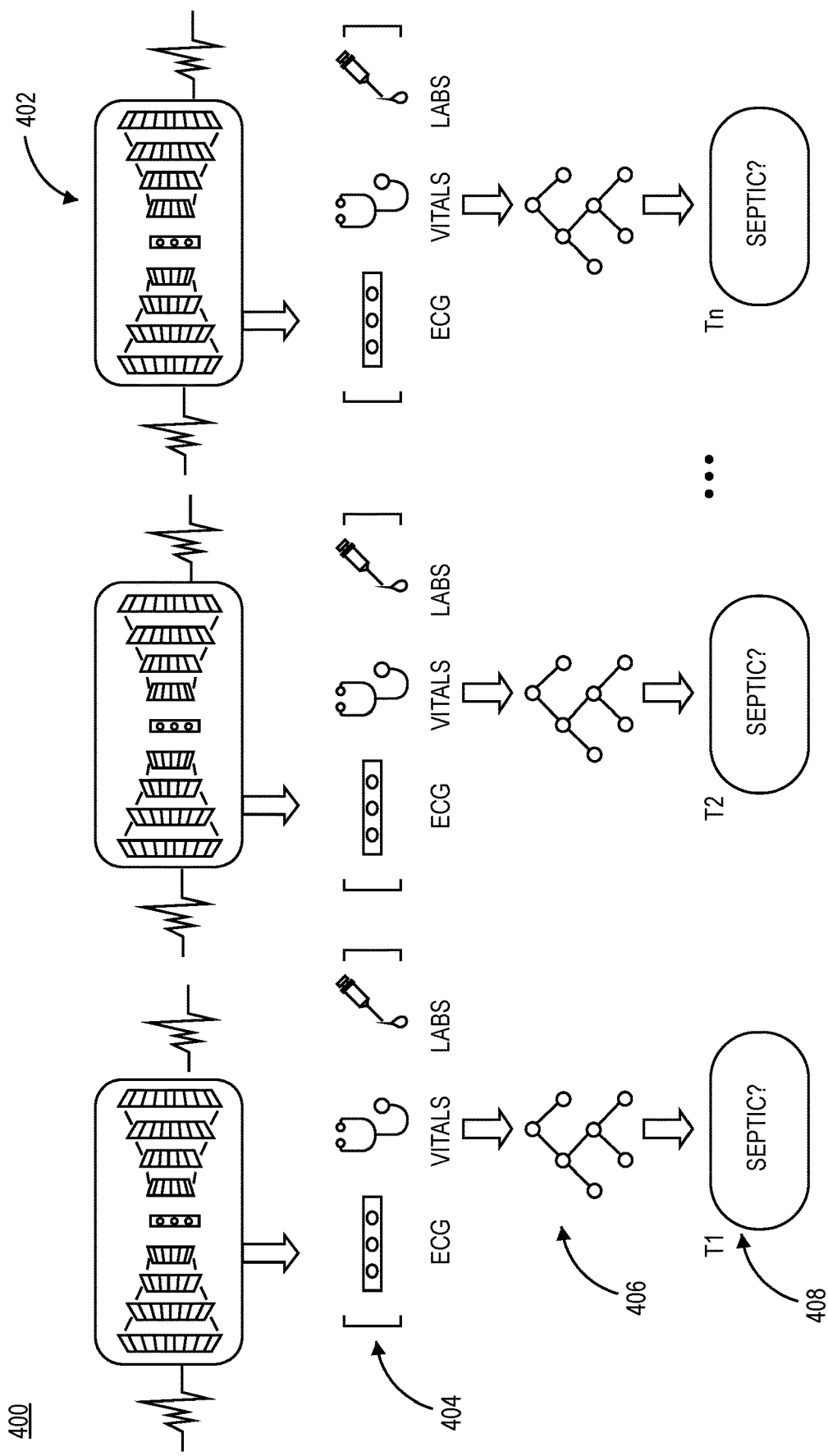
FIG. 4 depicts a block diagram of an exemplary coding architecture classifier, according to an embodiment.

FIG. 4 depicts an exemplary classifier 400. The classifier 400 may be applied to an input physiological signal (e.g., ECG and ABP signals) over a set of time steps T1 through Tn. At each time step, the coding architecture 402 may analyze ECG data. The coding architecture 402 may correspond to the coding architecture 100 of FIG. 1, in some embodiments. The coding architecture 402 may be a deep convolutional autoencoder or another type of coding architecture. The output of the coding architecture 402 may be an encoding (e.g., a compressed non-linear representation of the input physiological signal). The encoding may be joined at each time step into an input vector 404, along with EHR data (e.g., a lab data and/or a vital data) of the patient corresponding to the input signal. The input vector 404 may be input into a classification model such as gradient boosting tree 406 trained to predict the occurrence of a condition 408 within a time period (e.g., within three hours).

In an embodiment, the classifier 400 may be used to predict sepsis of a patient. The classifier 400 may receive ECG, ABP and/or PPG signals (e.g., from bedside monitors, a memory, a database, etc.). The classifier 400 may process the signals using a coding architecture such as the coding architecture 100 of FIG. 1. The classifier 400 may receive the embedded representations 106 of FIG. 1 and concatenate or otherwise join the embedded representations to lab and vital sign data corresponding to the patient. The joined data may be stored in a vector or other suitable data structure. For example, the classifier 400 may receive vital and/or lab information from a database. In some embodiments, the classifier 400 may include computer-executable instructions for receiving/retrieving patient data via a query wherein the query includes a patient identifier.

In an embodiment, the present techniques may include predicting medical sepsis in real-time, in advance of Sepsis-3 guidelines or obvious symptoms (e.g., hypotension). Patient data including a set of basic vitals and labs drawn may be used to train the classifier 400. The duration of each patient's hospital stay/encounter may be discretized into windows (e.g., three-hour windows) to normalize the number of data points per length of stay in the hospital. Sepsis-3 criteria may be applied to each window and the classifier 400 may be trained to identify the Sepsis-3 applied criteria target. The gradient-boosting tree 406 may be trained on common lab data (e.g. complete blood count, basic metabolic panel, lactate, etc.) and patient vital signs to predict when the patient will develop sepsis (e.g., within N minutes). Continuous physiological signals will provide feedback at a higher frequency than traditional interval vital signs or laboratory results alone. Additionally, because sepsis and septic shock are associated with important hemodynamic alterations, similar conditions can be identified in a lower-dimensional representation of the physiological signal. Therefore, the physiological signals will result in more information at a higher frequency than conventional techniques.

In an embodiment, the classifier 400 is implemented using a different classification model and/or architectures (e.g., an RNN model such as LSTM). An RNN may provide the additional benefit of capturing dependency between successive windows of time. The RNN may learn a set of hidden features that may then be used as input to the classification model 406.

In some embodiments, the window size of T1-Tn may be increased by concatenating embedded vectors together. In some embodiments, the coding architecture 402 may be used to learn an efficient representation of the EHR data.

Exemplary General Deterioration Classifier Embodiment

In an embodiment, the coding architecture 400 may be trained to predict the likelihood that a patient will deteriorate (e.g., develop shock, complications requiring ICU admission, need life-saving intervention such as vasopressor use/mechanical ventilation, etc.) within a period of time. The coding architecture 400 effectively represents a continuous signals (e.g. ECG, ABP, PPG) to predict general deterioration.

The coding architecture 400 may integrate heterogeneous data to predict deterioration. The coding architecture 400 may be merged with EHR data (e.g., laboratory results, vital signs, etc.) to create a predictive model of patient deterioration. Patient data may be labeled as with respect to condition prediction, however a positive label for deterioration may be applied when the patient deteriorated within a predetermined time of declining (e.g., within eight hours). Deterioration events may include ICU transfer, codes, valid rapid response team calls, cardiac arrest, administration of vasopressors, septic shock, mechanical ventilation, fluid and blood administration for resuscitation, and death. It will be appreciated by those of ordinary skill in the art that the integration of EHR with the techniques described herein advantageously increases the sensitivity and specificity of those techniques.

The present techniques may enable autoencoding of multiple simultaneous periodic variable physiological signals (e.g., an ECG signal, a pulse oximetry signal, etc.) and latter matching to predictive phenotypes. The multiple signal analysis may be synthesized with respect to a particular patient to obtain a greater overall view of the patient.

Exemplary Heart Failure Prediction Embodiment

In an embodiment, the coding architecture 400 uses ECG morphology to predict the onset of HF. The coding architecture 400 may analyze ECG morphology using a self-supervised approach.

In some embodiments, the coding architecture 400 may analyze time-domain characteristics of input physiological signals and may be combined with other information such as HRV features and EHR data. The present techniques may derive morphology features from an input physiological signal (e.g., an ECG). The present techniques may analyze the association of the morphology features, independently and in combination with other types of data (HRV features and EHR data) with the onset of HF. The present techniques may use the set of features to build a classification model for predicting HF incidence (e.g., a 12-month incidence). In some embodiments, the present techniques may identify premature ventricular contractions and atrial fibrillation rhythms which may be used as additional features for classification.

Exemplary Integrated Embodiment

In an embodiment, the present techniques may include a multi modal integrated system for predicting the onset of a disease. In the integrated system, multiple data sources (e.g., one or more of ECG, ABP, PPG, EHR, HRV and data from wearable sensors) may be used to more accurately predict the onset of a disease.

The integrated system may have sequential structure. A first model may use EHR codes to identify patients at high risk of the disease. A second model may analyze waveform morphology. A third model may analyze HRV. A module may integrate the respective outputs of the first, second and third models into a single model to further stratify high-risk patients in order to improve accuracy and reduce false positives.

In some embodiments, the module may assess physiologic waveform features extracted by the coding architecture (i.e., the embedded features), the HRV features and the EHR codes to determine the additive value of each output in relation to the prediction task. The features with the highest predictive power may be included in the integrated model.

Exemplary Machine Learning Computing Environment

Figure 5:
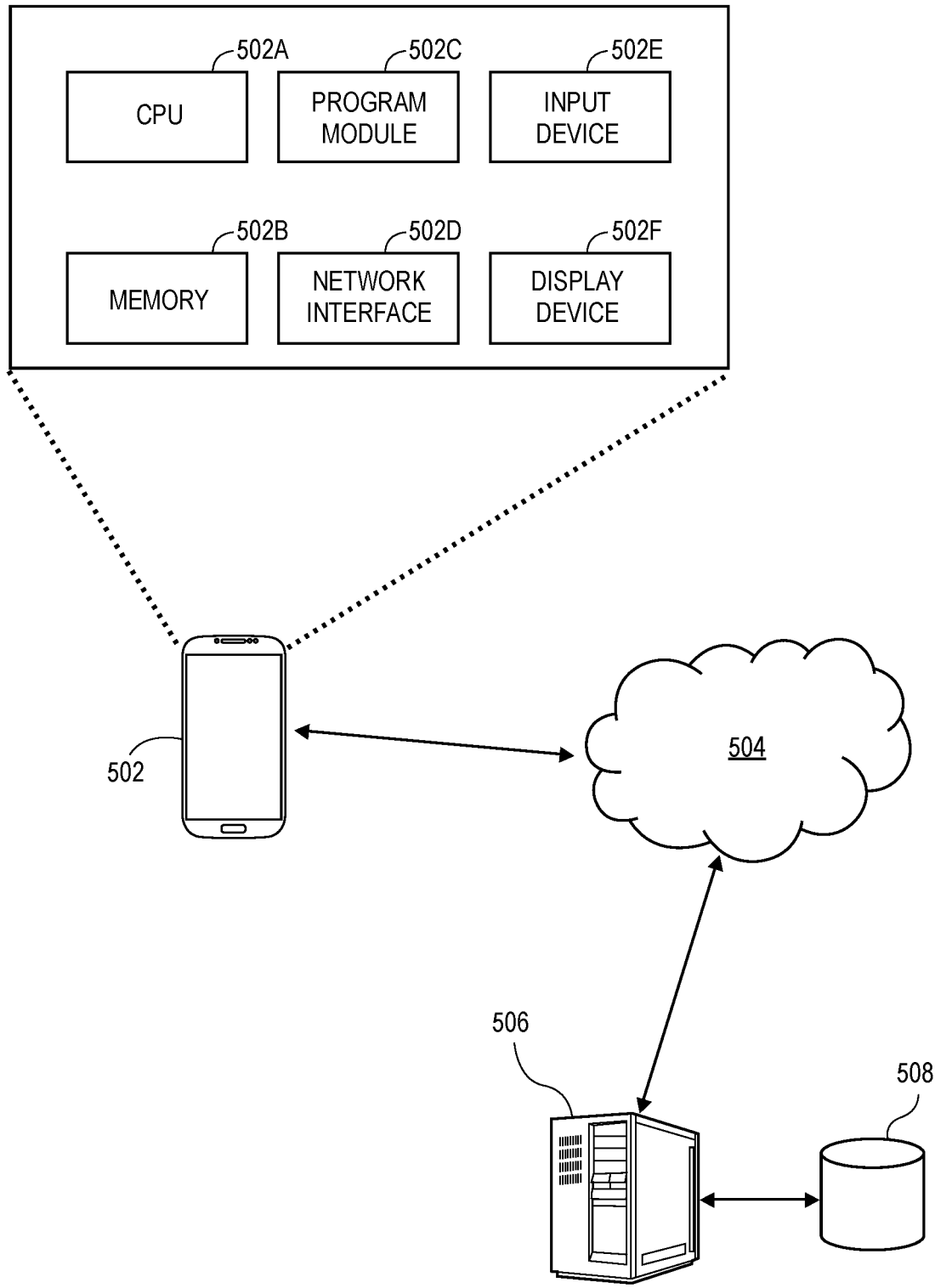
FIG. 5 depicts an exemplary machine learning computing environment in which the techniques disclosed herein may be implemented, according to an embodiment.

FIG. 5 depicts an exemplary machine learning computing environment 500 in which the techniques disclosed herein may be implemented, according to an embodiment.

The environment 500 includes a client computing device 502, a network 504, a computing device 506 and a database 508. Some embodiments may include a plurality of client computing devices 502, a plurality of remote computing devices 506 and/or a plurality of imaging device 508 that may be configured differently. For example, a first client computing device 502 may be an ECG machine used by the clinician to capture an input physiological signal corresponding to the patient according to the techniques discussed above with respect to FIG. 1-FIG. 4. A second client computing device 502 may be used by a physician to review the results of a machine learning analysis of the ECG input signal or other data (e.g., an output generated by an autoencoder and/or classifier). Multiple and/or separate networks may communicatively couple different components, such as the client computing device 502 and the remote computing device 502.

The client computing device 502 may be an individual server, a group (e.g., cluster) of multiple servers, or another suitable type of computing device or system (e.g., a collection of computing resources). For example, the client computing device 502 may be a mobile computing device (e.g., a server, a mobile computing device, a smart phone, a tablet, a laptop, a wearable device, etc.). In some embodiments the client computing device 502 may be a personal computing device of a user (e.g., a physician). The client computing device 502 may be communicatively coupled to the remote computing device 506 via the network 504 or by other means.

The client computing device 502 includes a processor 502A, a memory 502B, a program module 502C, a network interface controller (NIC) 502D, an input device 502E and a display device 502F.

The processor 502A may include any suitable number of processors and/or processor types, such as central processing units (CPUs) and one or more graphics processing units (GPUs). Generally, the processor 502A is configured to execute software instructions stored in the memory 502B.

The memory 502B may include one or more persistent memories (e.g., a hard drive/solid state memory) and stores one or more set of computer executable instructions/modules, including a machine learning training module and a machine learning operation module as described above. More or fewer modules may be included in some embodiments. In general, the modules included in the memory 502B include sets of computer-executable instructions for performing the present techniques. The modules may each be implemented using any suitable programming language (e.g., Python, C++, Java, etc.). In some embodiments, the modules included in the memory 502B may be implemented using web-based technologies and/or mobile applications (e.g., an Android or iPhone computing application).

The program module 502C may include one or more modules including respective sets of computer-executable instructions. The program module 502C may further include a set of computer-executable instructions for handling low-level communication for reading data from an ECG machine. For example, the low-level communication may include digital and/or analog (e.g., 12-lead) communication instructions.

In some embodiments, the program module 502C may include instructions for issuing notifications and/or alarms. The program module 502C may include the data collection module for receiving data from wearable devices. In some embodiments, the program module 502C may display one or more GUIs that allow the user to initiate a capture of input data, view information, and/or input feedback. For example, the program module 502C may allow the user to initiate capture of ECG signal data.

In other embodiments, the program module 502C may include an application that is used by a physician to view the results of a machine learning analysis. An output device may display information. For example, the client computing device 502 may be a tablet and the physician may open the application at the patient's bedside to review the output of the condition 208 as described with respect to FIG. 2.

The NIC 502D may include any suitable network interface controller(s), such as wired/wireless controllers (e.g., Ethernet controllers), and facilitate bidirectional/multiplexed networking over the network 504 between the client computing device 502 and other components of the environment 500 (e.g., another client computing device 502, the remote computing device 506, etc.).

The input device 502E may include any suitable device or devices for receiving input, such as one or more microphone, one or more camera, a hardware keyboard, a hardware mouse, a capacitive touch screen, etc. The display/output device 502F may include any suitable device for conveying output, such as a hardware speaker, a computer monitor, a touch screen, etc. In some cases, the input device 502E and the output device 502F may be integrated into a single device, such as a touch screen device that accepts user input and displays output.

The user may interact with the program module 502C via the input device 502E and/or the output device 502F. Specifically, the program module 502C may include computer-executable instructions that receive user input via the input device 502E and/or display one or more GUIs on the output device 502F. For example, the program module 502C may correspond to a mobile computing application (e.g., an Android, Phone, or other) computing application. The program module 502C may be a specialized application corresponding to the type of computing device embodied by the client computing device 502. For example, in embodiments where the client computing device 502 is a mobile phone, the mobile application module may correspond to a mobile application downloaded for an Phone. When the client computing device 502 is a tablet, the application module 532 may correspond to an application with tablet-specific features.

In some embodiments, one or more components of the computing device 502 may be embodied by one or more virtual instances (e.g., a cloud-based virtualization service). In such cases, one or more client computing device 502 may be included in a remote data center (e.g., a cloud computing environment, a public cloud, a private cloud, etc.). For example, a remote data storage module (not depicted) may remotely store data received/retrieved by the computing device 502.

The network 504 may include any suitable combination of wired and/or wireless communication networks, such as one or more local area networks (LANs), metropolitan area networks (MANs), and/or wide area network (WANs). As just one specific example, the network 504 may include a cellular network, the Internet, and a server-side LAN. As another example, the network 504 may support a cellular (e.g., 4G) connection to the client computing device 502, and an IEEE 802.11 connection to the remote computing device 506.

The client computing device 502 may be configured to communicate bidirectionally via the network 504 with the remote computing device 506. For example, the program module 502C may transmit captured data (e.g., ECG signals) and/or user requests to the remote computing device 506, and may receive/retrieve information (e.g., machine learning model outputs) from the remote computing device 506.

The remote computing device 506 may include a processor, a memory, and a NIC. The processor may include any suitable number of processors and/or processor types, such as one or more CPUs and/or one or more GPUs. Generally, the processor is configured to execute software instructions stored in the memory. The memory may include one or more persistent memories (e.g., a hard drive/solid state memory) and stores one or more set of computer executable instructions/modules, as discussed below.

For example, the remote computing device 506 may include the machine learning training module. The training module may include a set of computer-executable instructions for receiving/retrieving training data. The training data may include patient data that is labeled or unlabeled (e.g., historical ECG input signals). For example, the training data may correspond to the input data received by the input layer 102 of FIG. 1, the input vector 204 of FIG. 2, the input signal 302 of FIG. 3 and/or the input physiological signal 402 of FIG. 4, for example. The machine learning training module may receive/retrieve the training data from the database 508, for example. Once the machine learning training module has trained one or more machine learning models (e.g., the coding architecture 100 of FIG. 1), the machine learning training module may store the trained model in the database 508, the memory 502B, or another suitable location.

The remote computing device 506 may include the machine learning operation module. The machine learning operation module may include a set of computer-executable instructions for analyzing input data using one or more machine learning model trained by the machine learning training module. For example, the machine learning operation module may load a trained model into the memory 502B. The machine learning operation module may receive/retrieve input (e.g., the input signal 402 of FIG. 4) from the client 502. For example, the trained model may correspond to a coding architecture, an encoder (e.g., the encoder 404), a decoder (e.g., the decoder 308) and/or the classifier 408. The machine learning operation module may pass the input into the loaded trained machine learning model and receive output from the model. The machine learning operation module may analyze the output and perform one or more actions (e.g., send an email in response to a particular classification). The machine learning operation module may operate multiple trained models in a sequence as described herein. More or fewer modules may be included, in some embodiments.

The remote computing device 506 NIC may include any suitable network interface controller(s), such as wired/wireless controllers (e.g., Ethernet controllers), and facilitate bidirectional/multiplexed networking over the network 504 between the remote computing device 506 and other components of the environment 100 (e.g., another remote computing device 506, the client computing device 502, etc.).

The remote computing device 506 may be communicatively coupled to the database 508. The database 508 may be implemented as a relational database management system (RDBMS) in some embodiments. For example, the database 580 may include one or more structured query language (SQL) database, a NoSQL database, a flat file storage system, or any other suitable data storage system/configuration. In general, the database 508 allows the client computing device 502 and/or the remote computing device 506 to create, retrieve, update, and/or retrieve records relating to performance of the techniques herein.

For example, the database 508 allows the components of the environment 500 to store training data (e.g., ECG input signal data) and real-time input signals used for analysis. The database 508 may access training and pretraining data sets, EHR data, etc. The client 502 and/or remote computing device 506 may include respective sets of database drivers for accessing the database 508. In some embodiments, the database 508 may be located remotely from the remote computing device 506, in which case the remote computing device 506 may access the database 508 via the network 504.

The machine learning training module may include computer-executable instructions for training the one or more machine learning models as described above. In some embodiments, the model training module may incorporate one or more software libraries/frameworks (e.g., Google TensorFlow, Caffe, PyTorch, Keras, etc.) for model training. In some embodiments, the machine learning training module may use transfer learning techniques.

Once the machine learning training module has trained one or more machine learning models, the machine learning training module may serialize the trained models (including model weights) and store the models in the memory of the remote computing device 506 and/or in the database 508. The machine learning operation module, for example, may later deserialize the trained model and operate the deserialized model. Once the machine learning models are trained, the model operation module may operate the models to analyze ECG signals.

Specifically, the machine learning operation module may load the one or more trained models into memory, and operate the deep learning model as described above. For example, the models may be operated to classify a patient condition (e.g., AFib), and/or to remove noise from an ECG signal to improve the reliability and accuracy of an alarm system.

As noted, the present techniques may be used in embodiments that do and do not incorporate EHR. However, incorporating EHR may provide better model accuracy and allow experts and non-experts to make better diagnoses. It should be appreciated that the coding architecture model may be trained for additional use cases, using physiological signal inputs other than those produced by ECG machines. The present techniques provide advantages over conventional techniques, at least by reducing the number of false positives and false negatives in alarm systems.

Exemplary Computer-Implemented Methods

Figure 6:
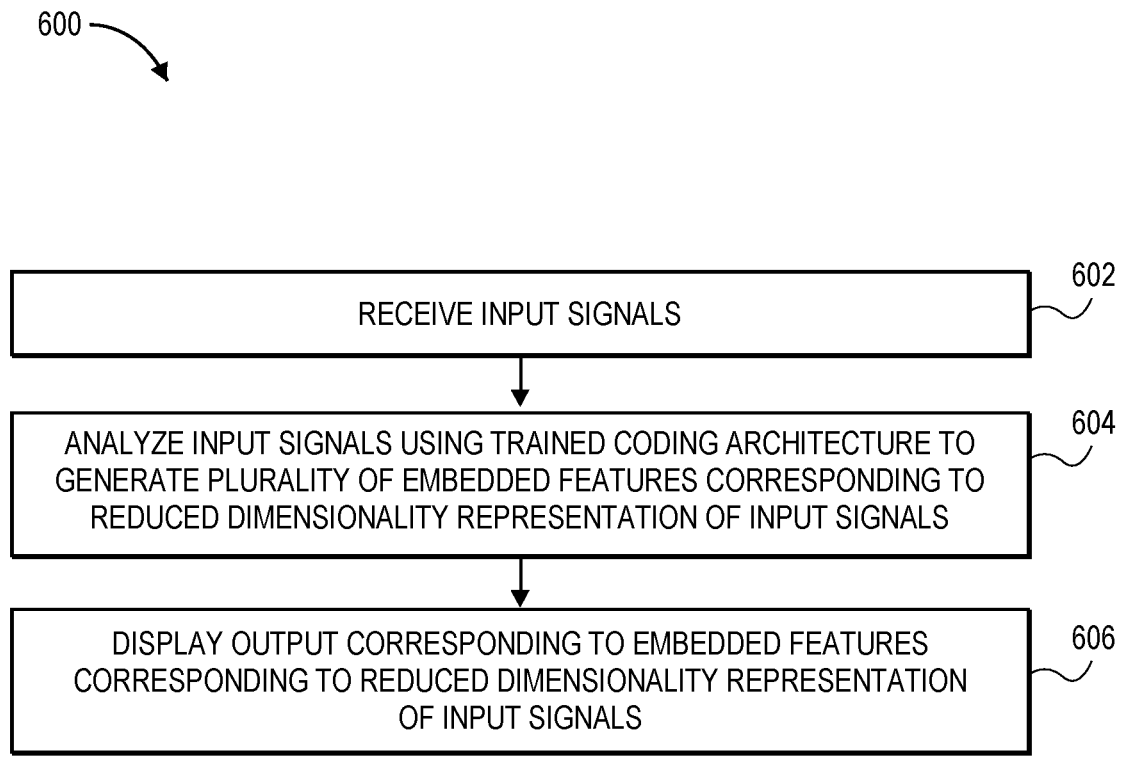
FIG. 6 depicts an exemplary computer-implemented method, according to one embodiment and scenario.

FIG. 6 depicts an exemplary computer-implemented method 600 for processing one or more raw input physiological signals corresponding to a patient to determine one or more condition corresponding to the patient. Specifically, as discussed herein, the method 600 may include receiving, via one or more processors, the input signals (block 602). For example, the method 600 may receive the input signals as raw variables via the input layer 102 of FIG. 1. The input signals may be received as the input vector 204 of FIG. 2. In some embodiments, the input signals may correspond to the input signal 302 of FIG. 3 and/or the input signal 402 of FIG. 4. The input signals may be received via a device such as the client device 502 of FIG. 5. For example, the client device 502 may be an ECG machine. The method 600 may include receiving input signals as periodic waveforms. The method 600 may include storing the input signals (e.g., in the memory 502B and/or the database 508). In some embodiments, the method 600 may process the input signals in real-time. In some embodiments, the method 600 may be performed in a client computing device (e.g., an ECG machine).

For example, the method 600 may include analyzing the input signal/waveforms to identify a disease or condition of the patient corresponding to (i) cardiac arrhythmia, (ii) myocardial infarction, (iii) myocardial ischemia, (iv) hemodynamic decompensation, (v) sepsis, (vi) trauma, (vii) acute respiratory failure and distress syndrome, or (viii) heart failure. It should be appreciated that the present techniques may include identification of other conditions/diseases, including without limitation, viral infections such as coronaviruses (e.g., severe acute respiratory syndrome (SARS), COVID-19 caused by SARS-CoV-2, etc.).

The method 600 may include analyzing, via the one or more processors, the input signals using a trained coding architecture to generate a plurality of embedded features corresponding to a reduced dimensionality representation of the input signals (block 604). For example, the method 600 may include analyzing the input signals using the encoding layers 104 of FIG. 1, as discussed above, to generate the embedded features 106. The method 600 may include analyzing the input signals using the encoder 304 of FIG. 3 or the encoder 404 of FIG. 4, to generate respectively, the compact representation 306 and the compact representation 406. The method 600 may include displaying an output corresponding to the embedded features corresponding to the reduced dimensionality representation of the input signals in an output device (block 606).

In some embodiments, the method 600 may include analyzing the plurality of embedded features corresponding to the reduced dimensionality representation of the input signals using a decoder comprising one or more decoding layers. For example, the method 600 may include processing the embedded features using the decoding layers 108 of FIG. 1 to generate the output signal 110. In some embodiments, the method 600 may include processing the compact representation 306 using the decoder 308 to generate the output 310, as discussed with respect to FIG. 3.

In still further embodiments, the method 600 may include analyzing the plurality of embedded features corresponding to the reduced dimensionality representation of the input signals using a classifier to identify a condition. For example, the classifier may correspond to the classifier 308 and the condition may correspond to the condition 310. In some embodiments, the classifier may analyze EHR information such as patient vitals, patient labs, etc. as discussed with respect to FIG. 2. The classifier may detect cardiac arrhythmia such as AFib and ventricular tachycardia, detect myocardial infarction or predict a condition such as sepsis, heart failure, etc. The classifier may use a technique such as a gradient boosted tree.

Exemplary Graphical User Interface Embodiments

Figure 7A:
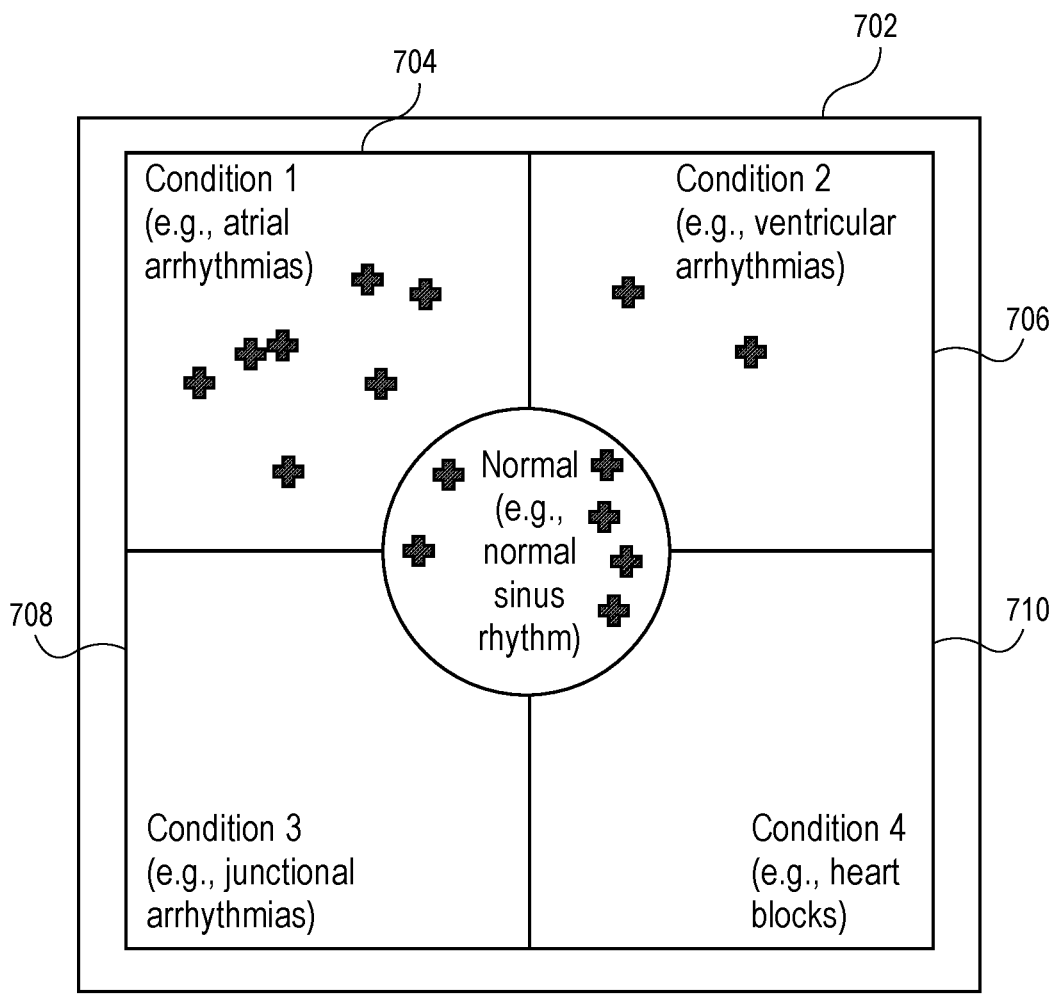
FIG. 7A depicts an exemplary graphical user interface for assisting clinical diagnosis and treatment, according to an embodiment.

In some embodiments, the present techniques may include one or more graphical user interface (GUI) for visualizing information, such as the compact representation of input signals (e.g., the embedded features 306 of FIG. 3). The present techniques may map higher dimensional inputs into lower dimensional outputs (e.g., two-dimensional outputs). For example, FIG. 7 depicts an exemplary graphical user interface 700 for assisting clinical diagnosis and treatment. The GUI 700 depicts a visualization 702 of embedded features. The visualization 700 includes a first sector 704 corresponding to a first condition (e.g., atrial arrhythmia). The visualization 702 includes a second sector 706 corresponding to a second condition (e.g., ventricular arrhythmia).

The visualization 702 includes a third sector 708 and a fourth sector 710 corresponding, respectively, to a third condition (e.g., junctional arrhythmia) and a fourth condition (e.g., a heart block). The visualization 702 includes a central region depicting a normal condition (e.g., a normal sinus rhythm). The GUI 700 depicts a plurality of markings each corresponding to the condition of a patient. Each of the plurality of markings relates to a time-based (e.g., minute by minute) assessment of the patient's condition. For example, the markings may correspond to embedded features as organized by a clustering algorithm (e.g., TSNE, PCA, etc.). Thus, the GUI 700 may be thought of as a visual representation of the embedded features, wherein a high-dimensional vector is mapped to a two-dimensional visual display. By plotting the embedded features, the present techniques advantageously allow diagnosticians to analyze embedded features corresponding to the patient, to find meaningful visual separation of different types of conditions (e.g., multiple arrhythmia). The GUI 700 may include one or more single or multi-dimensional (e.g., two-dimensional, three-dimensional, etc.) plots.

Figure 7B:
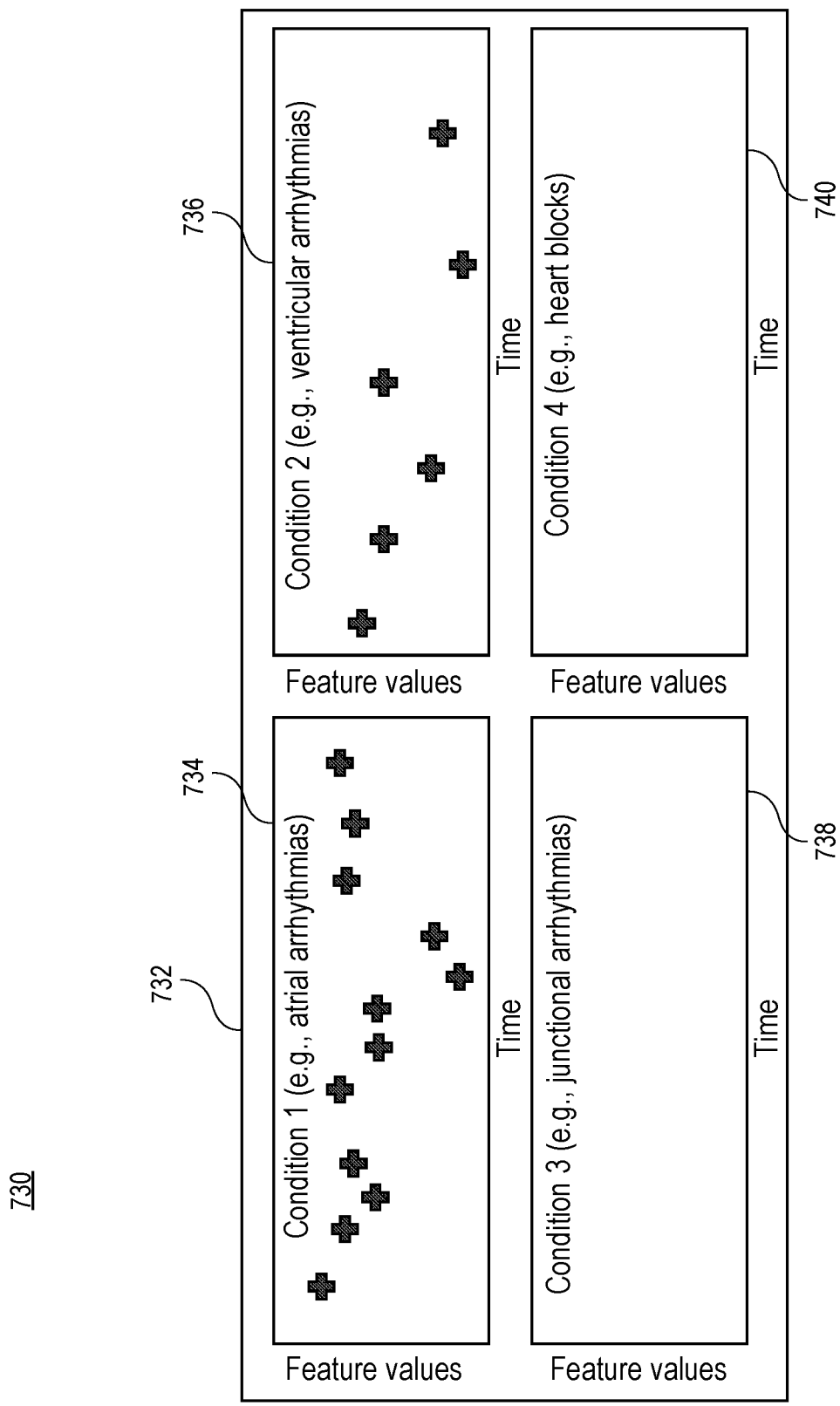
FIG. 7B depicts an exemplary graphical user interface for assisting clinical diagnosis and treatment, according to an embodiment.

FIG. 7B depicts an exemplary GUI 730 for assisting clinical diagnosis and treatment. The GUI 730 depicts a visualization 732 of embedded features. The visualization 732 includes a first sector 734 corresponding to a first condition (e.g., atrial arrhythmia). The visualization 732 includes a second sector 736 corresponding to a second condition (e.g., ventricular arrhythmia). The visualization 732 includes a third sector 738 and a fourth sector 740 corresponding, respectively, to a third condition (e.g., junctional arrhythmia) and a fourth condition (e.g., an heart block). In each of the sectors 734-740, feature values are plotted on the Y axis and time is plotted on the X axis. Markings are used to depict values. Thus, the GUI 700 may be analyzed by a diagnostician to determine aspects of the patient's health over time (e.g., the status of the patient, the direction of the patient's arrhythmia, etc.).

ADDITIONAL CONSIDERATIONS

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:

1. A computer-implemented method for processing one or more raw input physiological signals corresponding to a patient, the method comprising:
   receiving, via one or more processors, the raw input signals corresponding to a duration of time;
   analyzing, via the one or more processors, the raw input signals using a trained coding architecture to generate a plurality of embedded features corresponding to a reduced dimensionality representation of the raw input signals;
   wherein the trained coding architecture includes an encoder comprising one or more encoding layers; and
   displaying, via a graphical user interface, an output for assisting clinical diagnosis and treatment corresponding to the embedded features corresponding to the reduced dimensionality representation of the raw input signals in an output device, the output including a visualization of the embedded features having a plurality of sectors, each corresponding to a respective condition and each including a respective one or more feature markings organized by a clustering algorithm.

2. The computer-implemented method of claim 1, wherein the raw input signals correspond to periodic waveforms.

3. The computer-implemented method of claim 1, wherein analyzing the raw input signals using the trained coding architecture to generate the plurality of embedded features corresponding to the reduced dimensionality representation of the raw input signals includes generating at least one of i) a set of one or more morphological features, or ii) a set of one or more time/phase features.

4. The computer-implemented method of claim 1, further comprising:
   analyzing the plurality of embedded features corresponding to the reduced dimensionality representation of the raw input signals using a decoder comprising one or more decoding layers.

5. The computer-implemented method of claim 4,
   wherein the encoder is a first encoder comprising a first one or more encoding layers that transform the raw input signals into phase features, and
   wherein the trained coding architecture includes a second encoder comprising a second one or more encoding layers that transform the raw input signals into morphology features; and
   further comprising:
      transforming, via the decoder, the morphology features into single input period outputs corresponding to the raw input signals; and
      reconstructing the raw input signals by convolving the phase features and one or more single input period beats.

6. The computer-implemented method of claim 4, wherein the encoder is mapped by an aggregator to a set of embedded features; and
   further comprising:
      generating, via a distributor that maps the set of embedded features to the decoder, one or more sliding windows of an output signal, each corresponding to a respective sliding window of the raw input signals.

7. The computer-implemented method of claim 1, further comprising:
   analyzing the plurality of embedded features corresponding to the reduced dimensionality representation of the raw input signals using a classifier to identify a disease or condition of the patient.

8. The computer-implemented method of claim 1, further comprising:
   analyzing the plurality of embedded features corresponding to the reduced dimensionality representation of the raw input signals to identify a false alarm.

9. The computer-implemented method of claim 1, further comprising:
   analyzing other clinical or non-clinical information corresponding to the patient; and
   analyzing the plurality of embedded features corresponding to the reduced dimensionality representation of the raw input signals using a classification method.

10. The computer-implemented method of claim 1,
    wherein analyzing the raw input signals using the trained coding architecture to generate the plurality of embedded features corresponding to the reduced dimensionality representation of the raw input signals includes generating, via one or more processors, the reduced dimensionality representation by applying a t-Distributed Stochastic Neighbor Embedding (tSNE) algorithm, a Principal Component Analysis (PCA) algorithm or another dimensionality reduction algorithm to the embedded features; and
    further comprising:
       generating, via the one or more processors, the visualization of the embedded features.

11. A computing system comprising one or more processors; and one or more memories storing instructions that, when executed by the one or more processors, cause the computing system to:
    receive, via one or more processors, raw input signals corresponding to a duration of time;
    analyze, via the one or more processors, the raw input signals using a trained coding architecture to generate a plurality of embedded features corresponding to a reduced dimensionality representation of the raw input signals;
    wherein the trained coding architecture includes an encoder comprising one or more encoding layers; and
    display, via a graphical user interface, an output for assisting clinical diagnosis and treatment corresponding to the embedded features corresponding to the reduced dimensionality representation of the raw input signals in an output device
    the output including a visualization of the embedded features having a plurality of sectors, each corresponding to a respective condition and each including a respective one or more feature markings organized by a clustering algorithm.

12. The computing system of claim 11, wherein the raw input signals correspond to periodic waveforms.

13. The computing system of claim 11, the one or more memories including further instructions that, when executed by the one or more processors, cause the computing system to:
    analyze the plurality of embedded features corresponding to the reduced dimensionality representation of the raw input signals using a decoder comprising one or more decoding layers.

14. The computing system of claim 11, the one or more memories including further instructions that, when executed by the one or more processors, cause the computing system to:
    analyze the plurality of embedded features corresponding to the reduced dimensionality representation of the raw input signals using a classifier to identify a disease or condition of the patient.

15. The computing system of claim 11, the one or more memories including further instructions that, when executed by the one or more processors, cause the computing system to:
    analyze the plurality of embedded features corresponding to the reduced dimensionality representation of the raw input signals to identify a false alarm.

16. A non-transitory computer readable medium containing program instructions that when executed, cause a computer to:
    receive, via one or more processors, raw input signals corresponding to a duration of time;

analyze, via the one or more processors, the raw input signals using a trained coding architecture to generate a plurality of embedded features corresponding to a reduced dimensionality representation of the raw input signals;

wherein the trained coding architecture includes an encoder comprising one or more encoding layers; and display, via a graphical user interface, an output for assisting clinical diagnosis and treatment corresponding to the embedded features corresponding to the reduced dimensionality representation of the raw input signals in an output device, the output including a visualization of the embedded features having a plurality of sectors, each corresponding to a respective condition and each including a respective one or more feature markings organized by a clustering algorithm.

17. The non-transitory computer readable medium of claim 16 containing further program instructions that when executed, cause a computer to:

analyze the plurality of embedded features corresponding to the reduced dimensionality representation of the raw input signals using a decoder comprising one or more decoding layers.

18. The non-transitory computer readable medium of claim 16 containing further program instructions that when executed, cause a computer to:

analyze the plurality of embedded features corresponding to the reduced dimensionality representation of the raw input signals using a classifier to identify a disease or condition of the patient.

19. The non-transitory computer readable medium of claim 16 containing further program instructions that when executed, cause a computer to:

analyze the plurality of embedded features corresponding to the reduced dimensionality representation of the raw input signals to identify a false alarm.

20. The non-transitory computer readable medium of claim 16 containing further program instructions that when executed, cause a computer to:

analyze clinical or non-clinical information corresponding to the patient; and analyze the plurality of embedded features corresponding to the reduced dimensionality representation of the raw input signals using a classification model.

* * * * *